(12) United States Patent
Bhide et al.

(10) Patent No.: US 7,820,814 B2
(45) Date of Patent: *Oct. 26, 2010

(54) INHIBITORS OF KINASES

(75) Inventors: Rajeev S. Bhide, Princeton Junction, NJ (US); Zhen-Wei Cai, Belle Mead, NJ (US); Ligang Qian, Lawrenceville, NJ (US); Stephanie Barbosa, Lambertville, NJ (US); Louis Lombardo, Belle Mead, NJ (US); Jeffrey Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/399,429

(22) Filed: Mar. 6, 2009

(65) Prior Publication Data

US 2009/0170853 A1   Jul. 2, 2009

Related U.S. Application Data

(63) Continuation of application No. 11/832,976, filed on Aug. 2, 2007, now Pat. No. 7,521,450, and a continuation of application No. 11/035,248, filed on Jan. 13, 2005, now Pat. No. 7,265,113, and a continuation of application No. 10/623,171, filed on Jul. 18, 2003, now Pat. No. 6,869,952.

(60) Provisional application No. 60/397,256, filed on Jul. 19, 2002, provisional application No. 60/447,213, filed on Feb. 13, 2003.

(51) Int. Cl.
C07D 487/04   (2006.01)
A61K 31/53   (2006.01)
A61P 35/00   (2006.01)

(52) U.S. Cl. .................... 544/183; 514/243
(58) Field of Classification Search ............. 544/183; 514/243
See application file for complete search history.

(56) References Cited

U.S. PATENT DOCUMENTS

| | | | |
|---|---|---|---|
| 6,670,357 B2 | 12/2003 | Leftheris et al. | |
| 6,869,952 B2 * | 3/2005 | Bhide et al. | 514/243 |
| 6,916,815 B2 | 7/2005 | Vite et al. | |
| 6,933,386 B2 | 8/2005 | Bhide et al. | |
| 6,951,859 B2 | 10/2005 | Bhide et al. | |
| 6,969,717 B2 | 11/2005 | Bhide et al. | |
| 6,982,265 B1 | 1/2006 | Hunt et al. | |
| 7,030,118 B2 | 4/2006 | Lombardo et al. | |
| 7,034,151 B2 | 4/2006 | Chen et al. | |
| 7,112,675 B2 | 9/2006 | Hunt et al. | |
| 7,211,666 B2 | 5/2007 | Godfrey, Jr. et al. | |
| 7,244,733 B2 | 7/2007 | Hunt et al. | |
| 7,265,113 B2 * | 9/2007 | Bhide et al. | 514/243 |
| 7,521,450 B2 * | 4/2009 | Bhide et al. | 514/243 |
| 2004/0229877 A1 | 11/2004 | Leftheris et al. | |

FOREIGN PATENT DOCUMENTS

| | | |
|---|---|---|
| WO | WO 00/71129 | 11/2000 |
| WO | WO 02/40486 | 5/2002 |
| WO | WO 2004/009542 | 1/2004 |

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
Fan et al., Trend Pharcol. Sci., vol. 16, pp. 57-66 (1995).
Senger et al., Cancer and Metastasis Reviews, vol. 12, pp. 303-324 (1993).
DeVries et al., Science, vol. 255, pp. 989-991 (1992).
Terman et al., Biochem. Biophys. Res. Comm., vol. 187, pp. 1579-1586 (1992).
Jakeman et al., Endocrinology, vol. 133, pp. 848-859 (1993).
Kolch et al., Breast Cancer Research and Treatment, vol. 36, pp. 139-155 (1995).
Connolly et al., J. Biol. Chem., vol. 264, pp. 20017-20024 (1989).
Wolft Manfred E. "Burger's Medicinal Chemistry, 5ed, Part1", 1995, pp. 975-977.
Banker, G.S. et al., "Modern Pharmaceuticals, 3ed.", 1996, pp. 451 and 596.
West, Anthony R., "Solid State Chemistry and its Applications", 1988, pp. 358 & 365.
Vippagunta et al., Advanced Drug Delivery Reviews, vol. 48, pp. 3-26, 2001.
Cecil Textbook of Medicine, vol. 1, pp. 1004-1010 (1996).
Mass, R.D., Int. J. Radiation Oncology Bio. Phys., vol. 58, No. 3, pp. 932-940 (2004).
Fabbro et al., Pharmacology and Therapeutics, vol. 93, pp. 79-98 (2002).
Eskens, British Journal of Cancer, vol. 90, pp. 1-7 (2004).

(Continued)

Primary Examiner—Venkataraman Balasubramanian
(74) Attorney, Agent, or Firm—Elliott Korsen

(57) ABSTRACT

The present invention provides compounds of formula I,

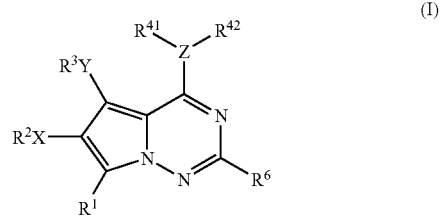

and pharmaceutically acceptable salts thereof.

The formula I compounds inhibit the tyrosine kinase activity of growth factor receptors such as VEGFR-2 and FGFR-1, thereby making them useful as anti-cancer agents. The formula I compounds are also useful for the treatment of other diseases associated with signal transduction pathways operating through growth factor receptors.

4 Claims, No Drawings

OTHER PUBLICATIONS

Milgliara et al., J. Heterocyclic. Chem., vol. 16, pp. 833-834 (1979).
Patil et al., J. Heterocyclic. Chem., vol. 31, pp. 781-786 (1994).
Folkman, Nature Medicine, vol. 1, pp. 27-31 (1995).
Cullinan-Bove et al., Endocrinology, vol. 133, pp. 829-837 (1993).
List of Results for search of: Brivanib; www.clinicaltrials.gov (Dec. 9, 2009).
"Angiogenesis and Vascular Endothelial Growth Factor (VEGF)"; slide kit provided by ResearchVEGF.com.

* cited by examiner

INHIBITORS OF KINASES

This is a continuation application of U.S. patent application Ser. No. 11/832,976 filed on Aug. 2, 2007, now U.S. Pat. No. 7,521,450, and U.S. patent application Ser. No. 11/035,248, filed on Jan. 13, 2005, now U.S. Pat. No. 7,265,113, and U.S. patent application Ser. No. 10/623,171, filed on Jul. 18, 2003, now U.S. Pat. No. 6,869,952, which claims the priority benefit of U.S. Provisional Application No. 60/397,256 filed Jul. 19, 2002 and No. 60/447,213 filed Feb. 13, 2003, the disclosures of which are incorporated herein by reference in their entirety.

FIELD OF THE INVENTION

This invention relates to compounds that inhibit the tyrosine kinase activity of growth factor receptors such as VEGFR-2, and FGFR-1, thereby making them useful as anticancer agents. The compounds are also useful in the treatment of diseases, other than cancer, which are associated with signal transduction pathways operating through growth factors and anti-angiogenesis receptors such as VEGFR-2.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, rheumatoid arthritis, atheroma, Kaposi's sarcoma and haemangioma, asthma, cancer and metastatic disease (Fan et al, 1995, Trend Pharmacol. Sci. 16: 57-66; Folkman, 1995, Nature Medicine 1: 27-31). Alteration of vascular permeability is thought to play a role in both normal and pathophysiological processes (Cullinan-Bove et al, 1993, Endocrinology 133: 829-837; Senger et al, 1993 Cancer and Metastasis Reviews, 12: 303-324).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised of the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity (DeVries et al, 1992, Science 255: 989-991; Terman et al, 1992, Biochem. Biophys. Res. Comm. 1992, 187: 1579-1586). Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. It is noted that aFGF and bFGF bind to and activate the receptor tyrosine kinase termed FGFR-1. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36: 139-155) and vascular permeability (Connolly et al, 1989, J. Biol. Chem. 264: 20017-20024).

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. It is now widely accepted that the ability of tumors to expand and metastasize is dependent upon the formation of this vascular network.

Binding of VEGF or bFGF to their corresponding receptor results in dimerization, autophosphorylation on tyrosine residues and enzymatic activation. These phosphotyrosine residues serve as "docking" sites for specific downstream signaling molecules and enzymatic activation results in EC activation. Disruption of these pathways should inhibit endothelial cell activation. Disruption of the FGFR-1 pathway should also affect tumor cell proliferation since this kinase is activated in many tumor types in addition to proliferating endothelial cells. Finally, recent evidence also suggests that disruption of VEGF signaling inhibits endothelial cell migration, a critical process in vascular network formation.

The over-expression and activation of VEGFR-2 and FGFR-1 in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

DETAILED DESCRIPTION OF THE INVENTION

In accordance with the present invention, compounds of formula I,

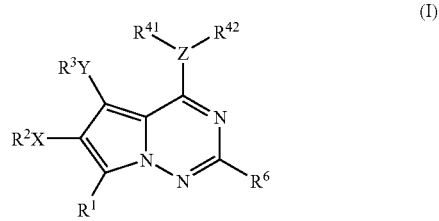

their enantiomers, diastereomers, and pharmaceutically acceptable salts, prodrugs and solvates thereof, inhibit the tyrosine kinase activity of growth factor receptors such as VEGFR-2. In formula I and throughout the specification, the above symbols are defined as follows:

Z is selected from the group consisting of O, S, N, OH, and Cl, with the provisos that when Z is O or S, $R^{41}$ is absent, and when Z is OH or Cl, both $R^{41}$ and $R^{42}$ are absent, and when Z is N, then $R^{41}$ is H;

X and Y are independently selected from the group consisting of O, OCO, S, SO, $SO_2$, CO, $CO_2$, $NR^{10}$, $NR^{11}CO$, $NR^{12}CONR^{13}$, $NR^{14}CO_2$, $NR^{15}SO_2$, $NR^{16}SO_2NR^{17}$, $SO_2NR^{18}$, $CONR^{19}$, halogen, nitro and cyano, or X or Y are absent;

$R^1$ is hydrogen, $CH_3$, OH, $OCH_3$, SH, $SCH_3$, $OCOR^{21}$, $SOR^{22}$, $SO_2R^{23}$, $SO_2NR^{24}R^{25}$, $CO_2R^{26}$, $CONR^{27}R^{28}$, $NH_2$, $NR^{29}SO_2NR^{30}R^{31}NR^{32}SO_2R^{33}$, $NR^{34}COR^{35}$, $NR^{36}CO_2R^{37}$, $NR^{38}CONR^{39}R^{40}$, halogen, nitro, or cyano;

$R^2$ and $R^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heteroaryl, substituted heteroaryl, heterocycloalkyl or substituted heterocycloalkyl; with the proviso that when X is halo, nitro or cyano, $R^2$ is absent, and, when Y is halo, nitro or cyano, $R^3$ is absent;

$R^6$ is H, alkyl, substituted alkyl, aryl, substituted aryl, heterocyclo, substituted heterocyclo, $NR^7R^8$, $OR^9$ or halogen;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{24}$, $R^{25}$, $R^{26}$, $R^{27}$, $R^{28}$, $R^{29}$, $R^{30}$, $R^{31}R^{32}$, $R^{34}$, $R^{35}$, $R^{36}R^{38}$, $R^{39}$ and $R^{40}$ are independently selected from the group consisting of hydrogen, alkyl, substituted alkyl, aryl, substituted aryl, heteroaryl, substituted heteroaryl, heterocyclo, or substituted heterocyclo;

$R^{22}$, $R^{23}$, $R^{33}$ and $R^{37}$ are independently selected from the group consisting of alkyl, substituted alkyl, aryl, substituted aryl, heteroaryl, substituted heteroaryl, heterocyclo, or substituted heterocyclo;

$R^{42}$ is

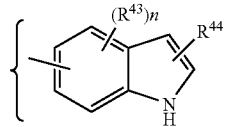

$(R^{43})_n$ wherein n equals 0, 1 or 2 and each $R^{43}$ is independently selected from the group consisting of hydrogen, fluorine, chlorine and methyl; and $R^{44}$ is methyl, or hydrogen, with the further provisos that:
a. $R^2$ may not be hydrogen if X is SO, $SO_2$, $NR^{13}CO_2$, or $NR^{14}SO_2$; and
b. $R^3$ may not be hydrogen if Y is SO, $SO_2$, $NR^{13}CO_2$, or $NR^{14}SO_2$ In a preferred embodiment $R^1$ is hydrogen or methyl; $R^6$ is hydrogen; $R^3$ is lower alkyl; and Z is oxygen or nitrogen.

In another preferred embodiment $R^1$ is hydrogen; $R^3$ is lower alkyl; Y is absent; X is oxygen or nitrogen; $R^{43}$ is fluoro or hydrogen; and $R^{44}$ is hydrogen or methyl.

In yet another preferred embodiment X is oxygen; $R^2$ is a substituted alkyl and $R^{43}$ is fluoro.

Preferred compounds of the invention include
4-(4-Fluoro-2-methyl-1H-indol-5-yloxy)-5-methylpyrrolo[2,1-f][1,2,4]triazin-6-ol, 1-[4-(4-Fluoro-2-methyl-1H-indol-5-yloxy)-5-methyl-pyrrolo[2,1-f][1,2,4]triazin-6-yloxy]-4-(aminosulfonyl)aminobutan-2-ol,
N-{3-[4-(4-Fluoro-2-methyl-1H-indol-5-yloxy)-5-methyl-pyrrolo[2,1-f][1,2,4]triazin-6-yloxy]-2-Hydroxy-propyl}-methanesulfonamide,
(2S)-3-[4-(4-Fluoro-2-methyl-1H-indol-5-yloxy)-5-methyl-pyrrolo[2,1-f][1,2,4]triazin-6-yloxy]-propane-1,2-diol,
(2R)-3-[4-(4-Fluoro-2-methyl-1H-indol-5-yloxy)-5-methylpyrrolo[2,1-f][1,2,4]triazin-6-yloxy]-propane-1,2-diol,
(2R)-1-[4-(4-Fluoro-2-methyl-1H-indol-5-yloxy)-5-methylpyrrolo[2,1-f][1,2,4]triazin-6-yloxy]-propan-2-ol,
(2S)-1-[4-(4-Fluoro-2-methyl-1H-indol-5-yloxy)-5-methylpyrrolo[2,1-f][1,2,4]triazin-6-yloxy]-propan-2-ol,
(2R)1-[4-(4-Fluoro-2-methyl-1H-indol-5-yloxy)-5-methylpyrrolo[2,1-f][1,2,4]triazin-6-yloxy]-3-methoxy-propan-2-ol,
(2S)-1-[4-(4-Fluoro-2-methyl-1H-indol-5-yloxy)-5-methylpyrrolo[2,1-f][1,2,4]triazin-6-yloxy]-3-methoxy-propan-2-ol,
2-[4-(4-Fluoro-2-methyl-1H-indol-5-yloxy)-5-methylpyrrolo[2,1-f][1,2,4]triazin-6-yloxy]-ethanol,
N-{2-[4-(4-Fluoro-2-methyl-1H-indol-5-yloxy)-5-methyl-pyrrolo[2,1-f][1,2,4]triazin-6-yloxy]-ethyl}-methanesulfonamide,
(2R)-1-[4-(4-Fluoro-2-methyl-1H-indol-5-yloxy)-5-methyl-pyrrolo[2,1-f][1,2,4]triazin-6-yloxy]-4-methanesulfonyl-butan-2-ol,
(2S)-1-[4-(4-Fluoro-2-methyl-1H-indol-5-yloxy)-5-methyl-pyrrolo[2,1-f][1,2,4]triazin-6-yloxy]-4-methanesulfonyl-butan-2-ol,
5-Methyl-4-(2-methyl-1H-indol-5-yloxy)-6-(3-piperidin-1-ylpropoxy)-pyrrolo[2,1-f][1,2,4]triazine,
4-(4-Fluoro-2-methyl-1H-indol-5-yloxy)-5-methyl-6-(2-piperidin-4-yl-ethoxy)-pyrrolo[2,1-f][1,2,4]triazine,
4-(4-Fluoro-2-methyl-1H-indol-5-yloxy)-5-methyl-6-(3-pyridin-4-yl-propoxy)-pyrrolo[2,1-f][1,2,4]triazine,
{1-[4-(4-Fluoro-2-methyl-1H-indol-5-yloxy)-5-methyl-pyrrolo[2,1-f][1,2,4]triazin-6-yloxymethyl]-3-methanesulfonyl-propyl}-dimethyl-amine, 71
2-[4-(4-Fluoro-2-methyl-1H-indol-5-yloxy)-5-methylpyrrolo[2,1-f][1,2,4]triazin-6-yloxy]-1-methylethylamine,
{2-[4-(4-Fluoro-2-methyl-1H-indol-5-yloxy)-5-methylpyrrolo[2,1-f][1,2,4]triazin-6-yloxy]-1-methylethyl}-methylamine,
4-(4-Fluoro-2-methyl-1H-indol-5-yloxy)-5-methyl-6-(morpholin-2-ylmethoxy)-pyrrolo[2,1-f][1,2,4]triazine,
[(1R),2S]-2-Dimethylaminopropionic acid-[2-[4-(4-fluoro-2-methyl-1H-indol-5-yloxy)-5-methylpyrrolo[2,1-f]-[1,2,4]triazin-6-yloxy]]-1-methylethyl ester,
[(1R),2S]-2-Amino-4-methylpentanoic acid-[2-[4-(4-fluoro-2-methyl-1H-indol-5-yloxy)-5-methylpyrrolo[2,1-f][1,2,4]triazin-6-yloxy]]-1-methylethyl ester,
[(1R),2S]-2-Aminopropionic acid 2-[4-(4-fluoro-2-methyl-1H-indol-5-yloxy)-5-methylpyrrolo[2,1-f][1,2,4]triazin-6-yloxy]-1-methylethyl ester,
4-(4-Fluoro-2-methyl-1H-indol-5-yloxy)-6-(3-methanesulfonyl-propoxy)-5-methyl-pyrrolo[2,1-f][1,2,4]triazine, and
N-{3-[4-(4-Fluoro-2-methyl-1H-indol-5-yloxy)-5-methyl-pyrrolo[2,1-f][1,2,4]triazin-6-yloxy]-propyl}-methanesulfonamide.

More preferred compounds of the invention are
4-(4-Fluoro-2-methyl-1H-indol-5-yloxy)-5-methylpyrrolo[2,1-f][1,2,4]triazin-6-ol,
(2-3-[4-(4-Fluoro-2-methyl-1H-indol-5-yloxy)-5-methyl-pyrrolo[2,1-f][1,2,4]triazin-6-yloxy]-propane-1,2-diol, (2R)-3-[4-(4-Fluoro-2-methyl-1H-indol-5-yloxy)-5-methylpyrrolo[2,1-f][1,2,4]triazin-6-yloxy]-propane-1,2-diol, (2R)-1-[4-(4-Fluoro-2-methyl-1H-indol-5-yloxy)-5-methylpyrrolo[2,1-f][1,2,4]triazin-6-yloxy]-propan-2-ol, (2S)-1-[4-(4-Fluoro-2-methyl-1H-indol-5-yloxy)-5-methylpyrrolo[2,1-f][1,2,4]triazin-6-yloxy]-propan-2-ol, (2R) 1-[4-(4-Fluoro-2-methyl-1H-indol-5-yloxy)-5-methylpyrrolo[2,1-f][1,2,4]triazin-6-yloxy]-3-methoxy-propan-2-ol, (2S)-1-[4-(4-Fluoro-2-methyl-1H-indol-5-yloxy)-5-methylpyrrolo[2,1-f][1,2,4]triazin-6-yloxy]-3-methoxy-propan-2-ol, 5-Methyl-4-(2-methyl-1H-indol-5-yloxy)-6-(3-piperidin-1-ylpropoxy)-pyrrolo[2,1-f][1,2,4]triazine, 4-(4-Fluoro-2-methyl-1H-indol-5-yloxy)-5-methyl-6-(2-piperidin-4-yl-ethoxy)-pyrrolo[2,1-f][1,2,4]triazine, 2-[4-(4-Fluoro-2-methyl-1H-indol-5-yloxy)-5-methylpyrrolo[2,1-f][1,2,4]triazin-6-yloxy]-1-methylethylamine,

[(1R),2S]-2-Dimethylaminopropionic acid-[2-[4-(4-fluoro-2-methyl-1H-indol-5-yloxy)-5-methylpyrrolo[2,1-f]-[1,2,4]triazin-6-yloxy]]-1-methylethyl ester,

[(1R),2S]-2-Amino-4-methylpentanoic acid-[2-[4-(4-fluoro-2-methyl-1H-indol-5-yloxy)-5-methylpyrrolo[2,1-f][1,2,4]triazin-6-yloxy]]-1-methylethyl ester,

[(1R),2S]-2-Aminopropionic acid 2-[4-(4-fluoro-2-methyl-1H-indol-5-yloxy)-5-methylpyrrolo[2,1-f][1,2,4]triazin-6-yloxy]-1-methylethyl ester, 4-(4-Fluoro-2-methyl-1H-indol-5-yloxy)-6-(3-methanesulfonyl-propoxy)-5-methyl-pyrrolo[2,1-f][1,2,4]triazine, and N-{3-[4-(4-Fluoro-2-methyl-1H-indol-5-yloxy)-5-methylpyrrolo[2,1-f][1,2,4]triazin-6-yloxy]-propyl}-methanesulfonamide.

The invention also provides a pharmaceutical composition comprising a compound of formula I or II and a pharmaceutically acceptable carrier.

The invention also provides a pharmaceutical composition comprising a compound of formula I or II in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxane; tamoxifen; toremifene; raloxifene; droloxifene; iodoxifene; megestrol acetate; anastrozole; letrozole; borazole; exemestane; flutamide; nilutamide; bicalutamide; cyproterone acetate; gosereline acetate; leuprolide; finasteride; metalloproteinase inhibitors; inhibitors of urokinase plasminogen activator receptor function; growth factor antibodies; growth factor receptor antibodies such as Avastin® (bevacizumab) and Erbitux® (cetuximab); tyrosine kinase inhibitors; serine/threonine kinase inhibitors; methotrexate; 5-fluorouracil; purine; adenosine analogues; cytosine arabinoside; doxorubicin; daunomycin; epirubicin; idarubicin; mitomycin-C; dactinomycin; mithramycin; cisplatin; carboplatin; nitrogen mustard; melphalan; chlorambucil; busulphan; cyclophosphamide; ifosfamide nitrosoureas; thiotepa; vincristine; Taxol® (pacliatxel); Taxotere® (docetaxel); epothilone analogs; discodermolide analogs; eleutherobin analogs; etoposide; teniposide; amsacrine; topotecan; flavopyridols; biological response modifiers and proteasome inhibitors such as Velcade® (bortezomib).

The invention also provides a method of inhibiting protein kinase activity of growth factor receptors which comprises administering to a mammalian species in need thereof, a therapeutically effective protein kinase inhibiting amount of a compound of formula I.

Additionally, there is disclosed a method of inhibiting tyrosine kinase activity of one or more growth factor receptor such as which comprises administering to a mammalian species in need thereof, a therapeutically effective amount of a compound of formula I or II. In a preferred embodiment said growth factor receptor is selected from the group consisting of VEGFR-2 and FGFR-1.

Finally, there is disclosed a method for treating a proliferative disease, comprising administering to a mammalian species in need thereof, a therapeutically effective amount of a compound of formula I. In a preferred embodiment the proliferative disease is cancer.

The following are definitions of terms used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole, indole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzimidazolyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclos, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991);

c) H. Bundgaard, *Advanced Drug Delivery Reviews*, 8, 1-38 (1992);

It should further be understood that solvates (e.g., hydrates) of the compounds of formula I are also within the scope of the present invention. Methods of salvation are generally known in the art.

Use and Utility

The present invention is based on the discovery that certain pyrrolotriazines are inhibitors of protein kinases. More specifically, they inhibit the effects of VEGF, a property of value in the treatment of disease states associated with angiogenesis and/or increased vascular permeability such as cancer. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung. In another embodiment, the compounds of the present invention are also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetes-induced renal disease), atheroma, arterial restenosis, autoimmune diseases, acute inflammation and ocular diseases with retinal vessel proliferation, diabetic retinopathy, retinopathy of prematurity and macular degeneration. The invention also relates to prevention of blastocyte implantation in a mammal, treatment of atherosclerosis, excema, sclerodema, hemangioma. Compounds of the present invention posses good activity against VEGF receptor tyrosine kinase while possessing some activity against other tyrosine kinases.

Thus according to a further aspect of the invention, there is provided the use of a compound of formula I, or a pharmaceutically acceptable salt thereof in the manufacture of a medicament for use in the production of an antiangiogenic and/or vascular permeability reducing effect in a mammalian animal such as a human being.

According to a further feature of the invention there is provided a method for producing an antiangiogenic and/or vascular permeability reducing effect in a mammalian animal, such as a human being, in need of such treatment which comprises administering to said animal an effective amount of a compound of formula I or a pharmaceutically acceptable salt thereof as defined herein before.

The compounds described herein also inhibit other receptor tyrosine kinases including HER1 and HER2 and are therefore useful in the treatment of proliferative disorders such as psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclinical and clinical studies. It is therefore expected that inhibitors of the HER1 and HER2 kinases will have efficacy in the treatment of tumors that depend on signaling from either of the two receptors. The ability of these compounds to inhibit HER1 further adds to their use as anti-angiogenic agents. See the following documents and references cited therein: Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639-2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904-914 (2000).

In addition, the formula I compounds of this invention may be used as contraceptives in mammals.

The antiproliferative, antiangiogenic and/or vascular permeability reducing treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example tamoxifen, toremifene, raloxifene, droloxifene, iodoxifene), progestogens (for example megestrol acetate), aromatase inhibitors (for example anastrozole, letrozole, borazole, exemestane), antihormones, antiprogestogens, antiandrogens (for example flutamide, nilutamide, bicalutamide, cyproterone acetate), LHRH agonists and antagonists (for example gosereline acetate, leuprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol® (paclitaxel), Taxotere® (docetaxel) and newer microtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols); biological response modifiers and proteasome inhibitors such as Velcade® (bortezomib).

As stated above, the formula I compounds of the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of kinases in the regulation of cellular proliferation in general, inhibitors can act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as VEGFR-2 and FGFR-1.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may also be administered as suspensions using carriers appropriate to this mode of administration. The compounds may be administered in a dosage range of about 0.05 to 300 mg/kg/day, preferably less than 200 mg/kg/day, in a single dose or in 2 to 4 divided doses.

Biological Assays

VEGFR-2 and FGFR-1 Kinase Assays

| Reagents | Final Concentration | |
|---|---|---|
| Stock Solution | VEGFR-2 | FGFR-1 |
| Tris pH 7.0 | 20 mM | 20 mM |
| BSA 10 mg/ml | 25 µg/ml | 25 □g/ml |
| $MnCl_2$ (1M) | 1.5 mM | 0.5 mM |
| $MgCl_2$ (1M) | — | 0.5 mM |
| DTT (1M) | 0.5 mM | 0.5 mM |
| Enzyme Stock in 10% glycerol (1 mg/ml) | 7.5 ng/rxn | 30 ng/rxn |
| Poly glu/tyr (10 mg/ml) | 75 µg/ml | 30 µg/ml |
| ATP (1 mM) | 2.5 µM | 1.0 µM |
| γ-ATP (10 µCi/µl) | 0.5 µCi/ml | 0.5 µCi/ml |

Incubation mixtures employed for VEGFR-2 or FGFR-1 assay contain the synthetic substrate poly glu/tyr, (4:1), ATP, ATP-γ-$^{33}$P and buffer containing $Mn^{++}$ and/or $Mg^{++}$, DTT, BSA, and Tris buffer. The reaction is initiated by addition of enzyme and after 60 minutes at room temperature is terminated by the addition of 30% TCA to a final concentration of 15% TCA. Inhibitors are brought to 10 mM in 100% DMSO. Assays are prepared in a 96 well format in quadruplicate. Compounds are diluted 1:500 in 100% DMSO and then 1:10 in water for a final DMSO concentration of 10%. 10 μL are added to rows B-H in a 96 well format of 10% DMSO. 20 μl of compound is added to row A at a concentration 5 fold higher than running conditions. Ten μL are transferred to each row followed by six serial dilutions with mixing, and at row F 10 μL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard Filter-Mate harvester. Activity is determined by quantitating the incorporated radioactivity using a Packard TopCount Microplate Scintillation Counter following the addition of Microscint-20 cocktail into each dried well of the UniFilter microplates.

The instant compounds inhibit VEGFR-2 and FGFR-1 kinases with $IC_{50}$ values between 0.001 to 10 μM. Preferred compounds have $IC_{50}$ values less than 0.3 μM.

These compounds are selective against VEGFR-2 and FGFR-1 kinase enzymes. They have minimum activity against HER-2, CDK kinases, LCK and Src kinases. Activity against these kinases is >2 μM.

Methods of Preparation

Certain compounds of formula I may be prepared according to the following schemes and the knowledge of one skilled in the art.

All temperatures are in degrees Celsius (° C.) unless otherwise indicated. Preparative Reverse Phase (RP) HPLC purifications were done on C18 reverse phase (RP) columns using water/methanol mixtures with 0.1% TFA as buffer solution. All of the synthesized compounds were characterized by at least proton NMR and LC/MS. During work up of reactions, the organic extract was dried over magnesium sulfate ($MgSO_4$), unless mentioned otherwise.

The following abbreviations are used for the commonly used reagents. NMM; N-methylmorpholine, DIBAL; diisobutylaluminum hydride, BOP reagent; benzotriazol-1-yloxy-tris(trimethylamino)phosphonium hexafluorophosphate, DCE; dichloroethane, $K_2CO_3$; potassium carbonate, KOH; potassium hydroxide, DCC; dicyclohexyl carbodiimide, EDCI; 1-(dimethylaminopropyl)-3-ethylcarbodiimide hydrochloride, RT; room temperature, HOBt; hydroxybenzotriazole, DCM; dichloromethane, CbzCl; chlorobenzoyl chloride, mCPBA; meta-chloroperbenzoic acid, $NaHCO_3$; sodium bicarbonate, HCl; hydrochloric acid, TFA; trifluoroacetic acid, $NH_4Cl$; ammonium chloride, DIPEA; diisopropylamine, $Et_3N$; triethylamine, $Na_2SO_4$; sodium sulfate, DEAD; diethyl azodicarboxylate, DPPA; diphenylphosphorylazide, DMF; dimethyl formamide, THF; tetrahydrofuran, Scheme 1

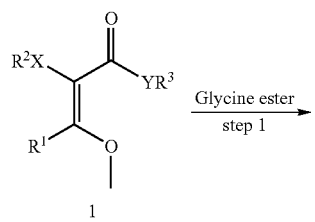

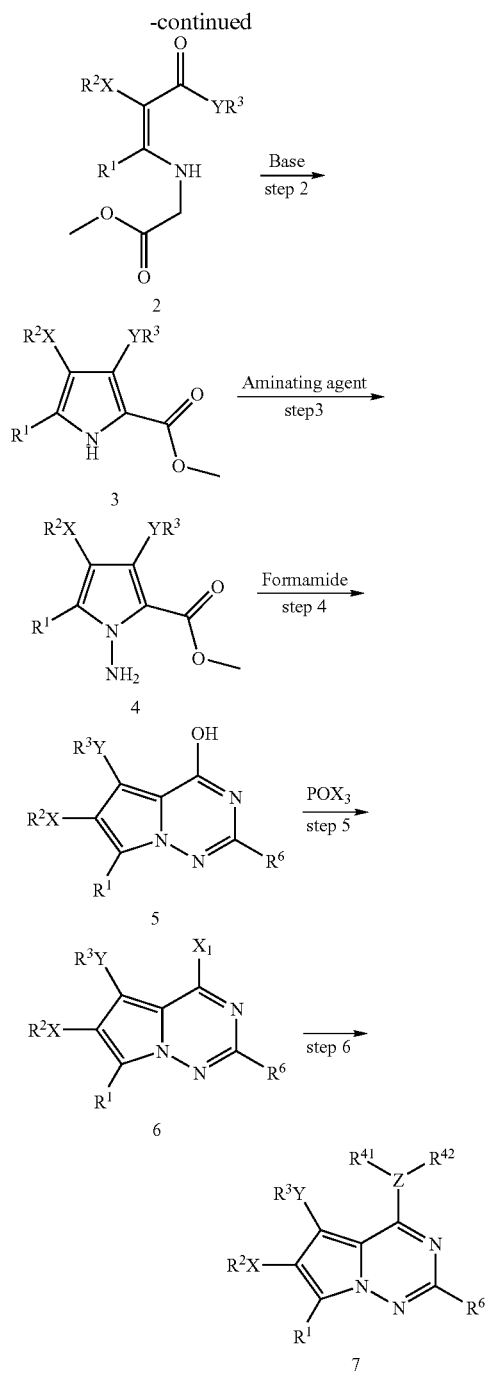

$X_1$ = halogen

Step 1

The first step is accomplished by the reaction of an optionally substituted malonate (1) such as where $XR^2$ is an ester and $YR^3$ is methyl, with a glycine ester in the presence of a mild base to obtain compound 2.

Step 2

Compound 2 of this scheme can then be cyclized in the presence of a base, such as potassium tert-butoxide, to obtain compound 3.

Step 3

The product 3 of this scheme is reacted with an aminating reagent, such as hydroxylamine-O-sulfonic acid or chloroamine, in the presence of a base such as KOH or sodium hydride to form the product 4.

Step 4

The compound 4 of this scheme is cyclized by treatment with formamide in the presence of a base such as sodium methoxide in MeOH with heating to form the product 5 of Scheme 1.

Step 5

The compound 5 of this scheme is halogenated, for example, with phosphorus oxychloride at elevated temperature, to form the product 6 of Scheme 1.

Step 6

The compound 6 is reacted with an amine such as an aniline, or a phenol, in an organic solvent, such as acetonitrile or DMF, to form the product 7 of Scheme 1.

Step 2

The compound 2 of this scheme can then be treated with a peroxide such as hydrogen peroxide or sodium perborate in the presence of a Lewis acid, such as boron trifluoride, at low temperature to afford phenolic compound 3 of Scheme 2.

Step 3

Alkylation of the phenolic group of compound 3 of this scheme with an alkylating agent such as bromoethane in the presence of a base, such as sodium hydride would afford compound 4 of Scheme 2. Alternatively, compound 3 can be treated with an alcohol under Mitsunobu conditions where in compound 3 and an alcohol are stirred in the presence of triphenyl phosphine and DEAD to obtain compound 4 of Scheme 2.

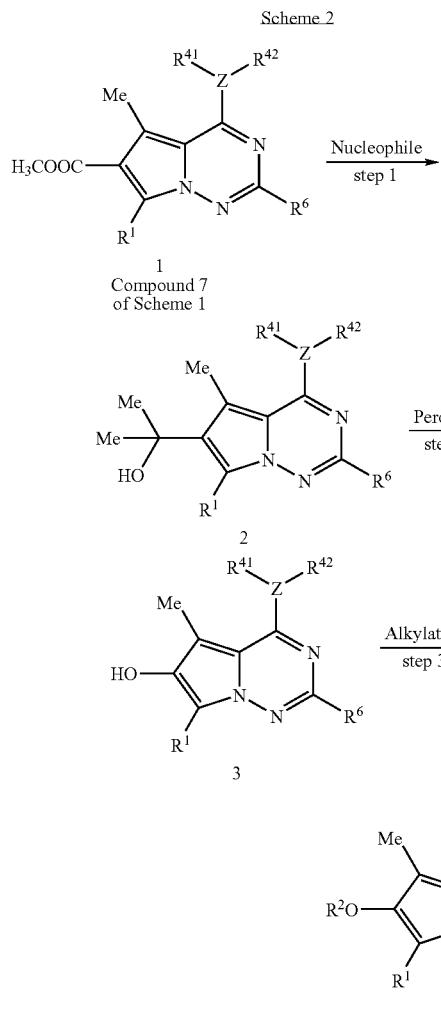

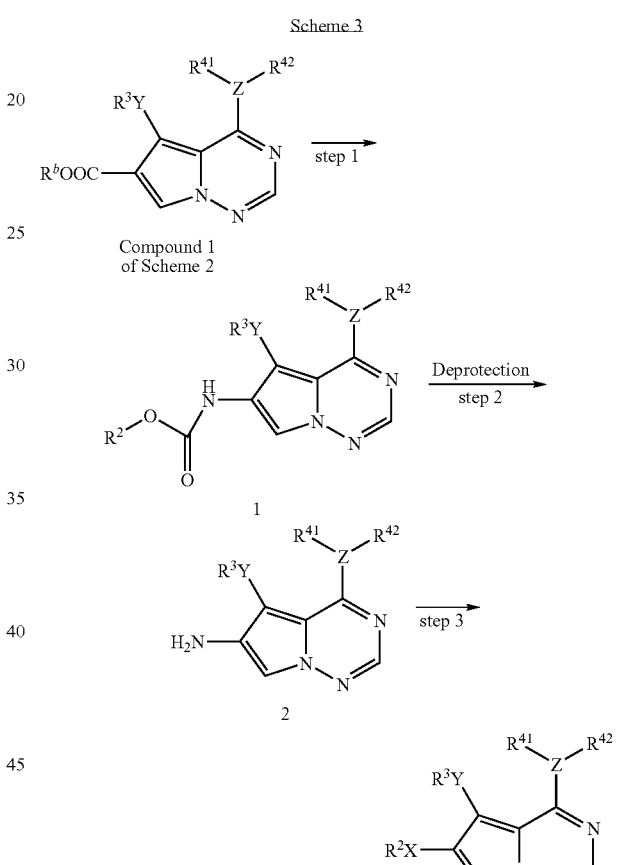

wherein $X = NR^{10}$, $NR^{11}CO$, $NR^{12}CONR^{13}$, $NR^{14}COO$, $NR^{15}SO_2$, $NR^{16}SO_2NR^{17}$, as described hereinbefore.

Step 1

Compound 1 of Scheme 2 is converted to carboxylic acid by treatment with a base such as aqueous KOH. This acid undergoes Curtius rearrangement by treatment with diphenyl phosphoryl azide in the presence of an alcohol, such as benzyl alcohol, in an organic solvent, such as 1,4-dioxane, to afford compound 1 of this scheme.

Step 2

Deprotection of the carbamate group is achieved, when optionally protected by groups such as carbobenzyloxy (Cbz), by hydrogenation over a catalyst, such as palladium to afford compound 2 of this scheme.

Step 1

A compound 7 of Scheme 1 wherein $YR^3$ is an alkyl group, such as methyl, and $XR^2$ group is an ester, can be treated with a nucleophile such as methyl magnesium bromide or methyl magnesium chloride, at low temperatures to afford compound 2 of Scheme 2.

Step 3

The amino group of compound 2 of this scheme is acylated, for example, by treatment with a carboxylic acid in the presence of a coupling agent such as DCC, or is sulfonylated, for example, by treatment with a sulfonyl chloride. Alternatively, the amino group of compound 2 of this scheme is alkylated with alkyl halides or undergoes reductive amination with aldehydes in the presence of a reducing agent, such as sodium cyanoborohydride or sodium borohydride.

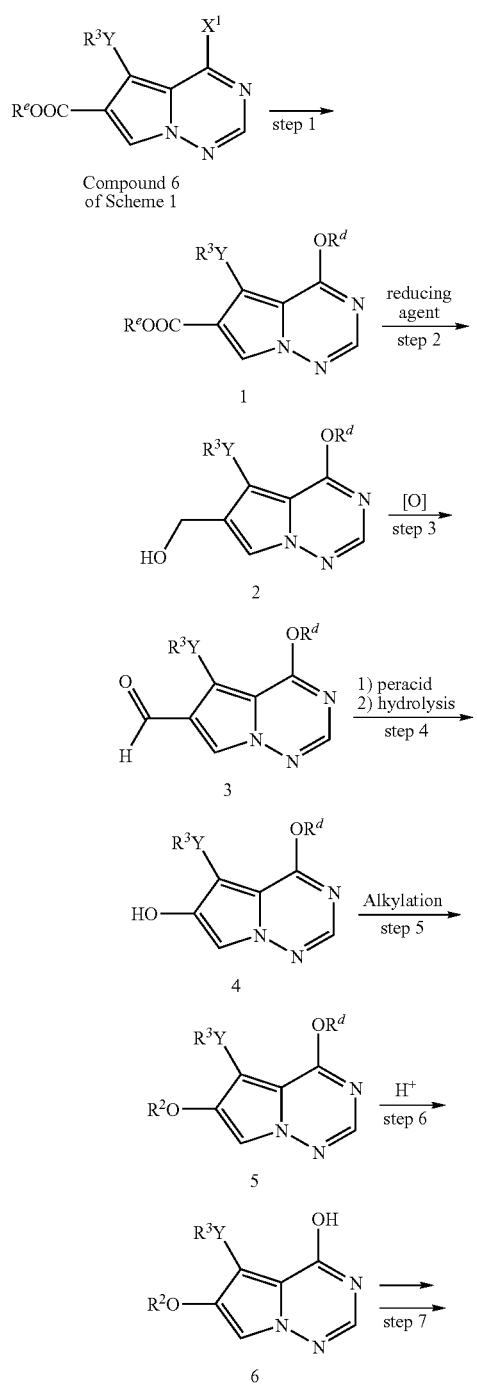

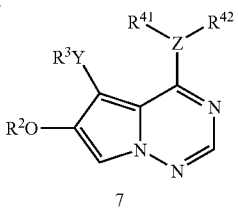

$X^1$ = halogen
$R^d$ = $R^e$ = $R^6$ described hereinabove

Step 1

Compound 6 of Scheme 1 is converted to an ether (etherified) at the 4-position, for example, by treatment with phenoxide or methoxide anion.

Step 2

Reduction with a reducing agent, such as diisobutylaluminum hydride (DIBAL), in an organic solvent, such as toluene, affords the alcohol 2 of this scheme.

Step 3

Oxidation of the alcohol is achieved by treatment of compound 2 of this scheme, for example, with manganese dioxide ($MnO_2$) at an elevated temperature in an organic solvent, such as toluene.

Step 4

Treatment of compound 3 of this scheme with an oxidant, such as m-chloroperbenzoic acid (m-CPBA), in an organic solvent, such as dichloromethane (DCM), followed by aqueous hydrolysis with a base, such as potassium bicarbonate, affords the hydroxyl compound 4.

Step 5

Alkylation of the phenol group in compound 4 with an electrophilic agent, such as iodomethane, in the presence of a base, such as NaH, at from 0° C. to 100° C., affords compound 5.

Step 6

Hydrolysis of compound 5 of this scheme is achieved by treatment with an acid, such as aqueous HCl, at an elevated temperature, to afford compound 6.

Step 7

Compound 6 of this scheme is converted to compound 7 using procedures analogous to those described in Scheme 1.

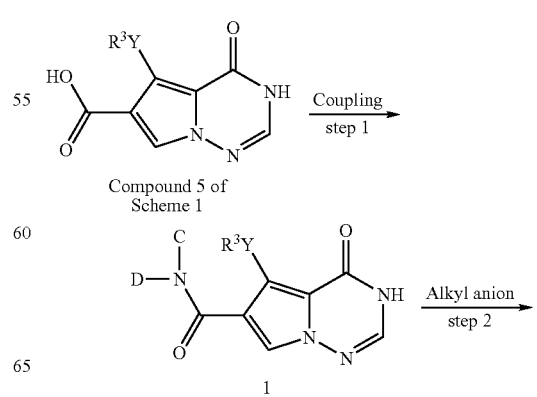

-continued

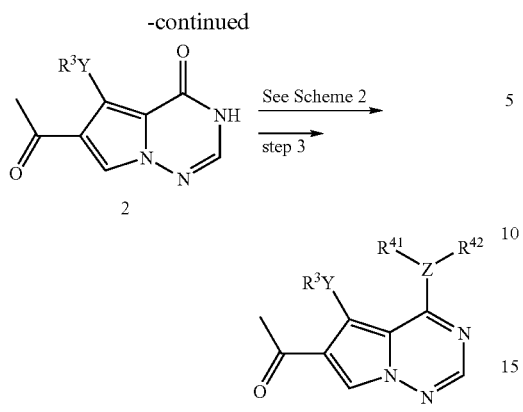

C, D = Me, OMe, NHNH₂, H, independently

Step 1

Compound 5 of Scheme 1 in which XR²=carboxylic acid, can be treated with an amine such as ammonia, N,O-dimethylhydroxylamine or substituted hydrazine in the presence of a coupling agent, such as dicyclohexylcarbodiimide (DCC) to obtain compound 1 as an amide or a hydrazide.

Step 2

When the amine used in Step 1 is N,O-dimethylhydroxylamine, the resulting compound can be treated with an alkylating agent such as methyllithium, to obtain compound 2.

Step 3

Compound 2 of this scheme then can be converted to compound 3 as described in Scheme 1.

Scheme 6

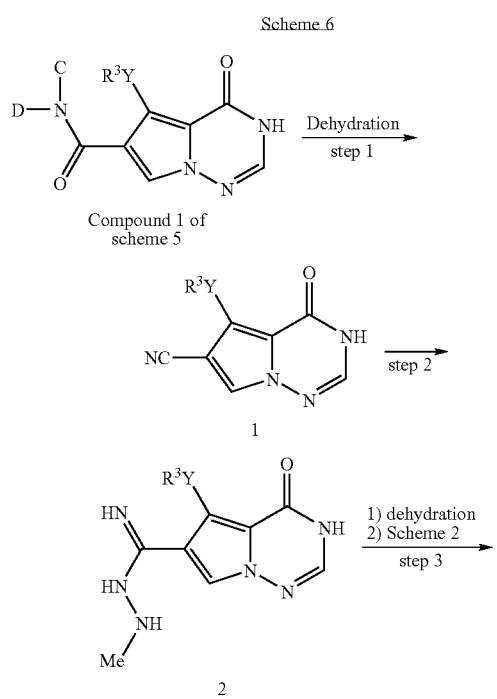

-continued

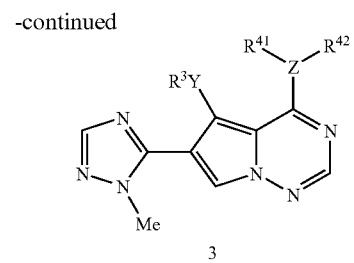

C, D = Me, OMe, NHNH₂, H, independently

Step 1

When the amine used in Step 1 of Scheme 5 is ammonia, the resulting compound can be treated with a dehydrating agent such as phosphorous oxychloride, to obtain compound 1.

Step 2

The compound 1 of this scheme can then be treated with a strong acid such as sulfuric acid in an alcohol such as ethanol to obtain an imidate which then can be treated with a substituted hydrazine, such as methylhydrazine, to obtain compound 2.

Step 3

The compound 2 of this scheme can then be treated with a dehydrating agent such as phosphorous oxychloride, to obtain an intermediate chloroimidate which when treated further with an appropriate aniline or phenol can afford compound 3 of this scheme as described in scheme 1.

Scheme 7

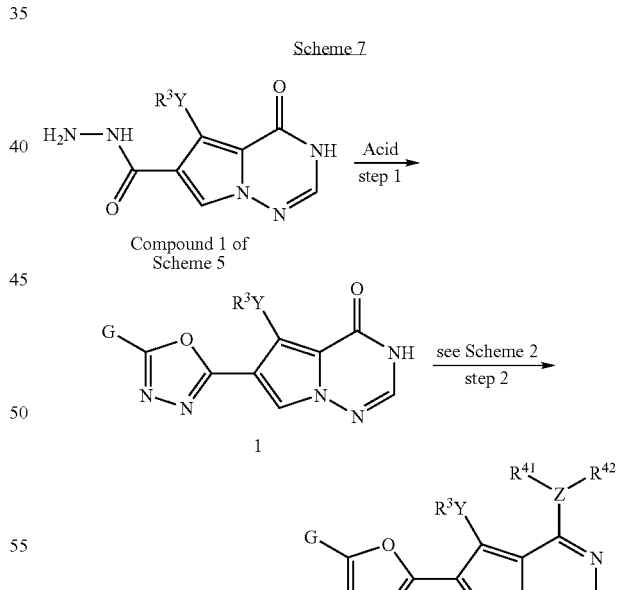

G = substituted methyl or methylene or substituted nitrogen or substituted suflur etc.

Step 1

When the amine used in Step 1 of Scheme 5 is hydrazine, the resulting compound can be treated with an acid such as difluoroacetic acid in the presence of a dehydrating agent such as phosphorous oxychloride, or a substituted acetimidic ester or phosgene imidinium chloride to obtain compound 1.

Step 2

The compound 1 can be then converted to compound 2 as described before in Scheme 2.

In addition, other compounds of formula I may be prepared using procedures generally known to those skilled in the art. In particular, the following examples provide additional methods for preparing compounds of this invention.

The invention will now be further described by the following working examples, which are preferred embodiments of the invention. These examples are illustrative rather than limiting, and it is to be understood that there may be other embodiments that fall within the spirit and scope of the invention as defined by the claims appended hereto.

Example 1

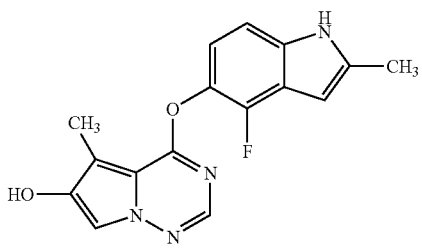

4-(4-Fluoro-2-methyl-1H-indol-5-yloxy)-5-methylpyrrolo[2,1-f][1,2,4]triazin-6-ol A. 4-Chloro-5-methylpyrrolo[2,1-f][1,2,4]triazine-6-carboxylic Acid Ethyl Ester A mixture of 4-hydroxy-5-methylpyrrolo[2,1-f][1,2,4]triazine-6-carboxylic acid ethyl ester (60.0 g, 271.2 mmol, for preparation see WO 0071129), phosphorus oxychloride (30.3 mL, 325.4 mmol) and diisopropylethyl amine (37.7 mL, 217 mmol) in toluene (800 mL) was heated to reflux under argon for 18 h and then cooled to room temperature. The mixture was concentrated on rotovap and the residue was diluted with dichloromethane (1000 mL) and cold sodium bicarbonate solution (300 mL). The resulting mixture was stirred at room temperature for 10 min. The separated organic layer was washed with cold brine (300 mL), dried, and concentrated in vacuo. The crude material was purified by chromatography on silica gel eluting with dichloromethane to provide the desired compound (64.8 g, 99%) as a yellow solid.

B. 4-Ethoxy-5-methylpyrrolo[2,1-f][1,2,4]triazine-6-carboxylic Acid Ethyl Ester

To a solution of compound A of this example (23 g, 96 mmol) in tetrahydrofuran (0.6 L) under argon at 0° C. was added sodium ethoxide in ethanol (21% w/w, 43 mL, 115.2 mmol) dropwise over 20 min. The reaction was stirred at 0° C. for 1 hr, diluted with ethyl acetate and washed with ammonium chloride solution and brine. The organic layer was dried, concentrated and the residue was purified by chromatography on silica gel eluting with dichloromethane followed by 50% ethyl acetate in hexanes to provide the desired compound (23.5 g, 98%) as a white solid. LC/MS; $(M+H)^+=250.17$ C. 2-(4-Ethoxy-5-methylpyrrolo[2,1-f][1,2,4]triazin-6-yl)-propan-2-ol To a solution of compound B of this example in THF (2.5 L) at 0° C. was slowly added methyl magnesium bromide (3M in $Et_2O$, 360 mL, 1.08 mol) with addition funnel. The mixture was allowed to warm to room temperature, whereupon stirring was continued for 4 h. The reaction was quenched by ammonium chloride solution and extracted with ethyl acetate. The organic layer was washed with sodium chloride solution and dried, to afford the desired compound (78 g, 100%) as a yellow solid. LC/MS; $(M+H)^+=236.1$ D. 4-Ethoxy-5-methylpyrrolo[2,1-f][1,2,4]triazin-6-ol A mixture of hydrogen peroxide (30%, 10.3 mL, 178.5 mmol) and boron trifluoride diethyl etherate (271.4 mL, 2.14 mol) was stirred at 0° C. for 30 min. It was then cooled to −20° C. and a solution of Compound C of this example (30 g, 129.5 mmol) in dichloromethane (1.45 L) at −15° C. was added. The reaction mixture reached −3° C., and then cooled to −40° C. To this mixture was added a saturated solution of sodium sulfite with stirring. The resulting mixture was extracted with ethyl acetate, dried, and concentrated in vacuo to provide Compound D (26 g, 76%). LC/MS; $(M+H)^+=194.2$ E. 6-Benzyloxy-4-ethoxy-5-methylpyrrolo[2,1-f][1,2,4]triazine A mixture of compound D of this example (1 g, 5.2 mmol), benzyl bromide (0.62 mL, 5.2 mmol) and potassium carbonate (2.1 g, 15.5 mmol) in dimethyl formamide (10 mL) was stirred at room temperature for 12 h. The reaction was diluted with ethyl acetate and washed with water, 10% lithium chloride solution and brine. The organic layer was dried ($Na_2SO_4$) and concentrated in vacuo to give Compound E (1 g) as yellow solid which was used without further purification for the next step.

F. 6-Benzyloxy-5-methylpyrrolo[2,1-f][1,2,4]triazin-4-ol

Compound E of this example (90 g, crude) in 1N HCl (600 mL) and ethanol (800 mL) was heated to reflux for 4 h. A solid precipitated which was collected by filtration, washed with a mixed solvent (water/ethanol/methanol=4/4/2) and dried to give a off-white solid, which was washed with dichloromethane to afford Compound F (65 g) as a white solid. LC/MS; $(M+H)^+=256.2$ G. 6-Benzyloxy-4-chloro-5-methylpyrrolo[2,1-f][1,2,4]triazine A mixture of compound F of this example (10 g, 39.2 mmol), phosphorus oxychloride (4.4 mL, 47.1 mmol) and diisopropylethyl amine (5.5 mL, 31.4 mmol) in toluene (150 mL) was stirred at 85° C. for 2 h and then more phosphorus oxychloride (1.1 mL, 11.8 mmol) was added. After 2 h, additional phosphorus oxychloride (1.1 mL, 11.8 mmol) was added. The reaction mixture was continuously stirred at 85° C. for 1 h and then concentrated. The residue was dissolved in dichloromethane, washed with cold sodium bicarbonate solution, dried, and concentrated in vacuo. The crude material was purified by chromatography on silica gel eluting with dichloromethane to provide Compound G (9.9 g, 93%) as a yellow solid.

H. 6-Benzyloxy-4-(4-fluoro-2-methyl-1H-indol-5-yloxy)-5-methylpyrrolo[2,1-f][1,2,4]triazine A solution of 4-fluoro-2-methyl-1H-indol-5-ol (6.47 g, 39.2 mmol, for preparation see below) in dimethyl formamide (100 mL) was degassed with argon and then cooled to −20° C. Sodium hydride (60% in oil, 1.57 g, 39.2 mmol) was added in one portion. The reaction mixture was allowed to warm to 0° C. with stirring over 30 min, cooled back to −20° C. and a solution of Compound G of this example in dimethyl formamide (100 mL) was added in one portion. The reaction was warmed to room temperature. After 30 min, the mixture was acidified with 1N HCl (200 mL), diluted with ethyl acetate (1.8 L), and washed with a 10% lithium chloride solution (0.4 L×2), 1N NaOH solution (0.3 L×2), buffer (pH=2, 200 mL), and NaCl solution (0.4 L). The organic layer was dried, and concentrated in vacuo to provide Compound H (15 g, 95%) as a tan solid. LC/MS; (M+H)$^+$=403.1

I. 4-(4-Fluoro-2-methyl-1H-indol-5-yloxy)-5-methylpyrrolo[2,1-f][1,2,4]triazin-6-ol A mixture of Compound H of this example (15 g, 37.3 mmol), ammonium formate (12 g, 190 mmol) and Pd/C (10%, 1.5 g) in dimethyl formamide (100 mL) was stirred at room temperature for 2 h. The mixture was filtered through Celite® and the filtrate was diluted with ethyl acetate and washed successively with 10% lithium chloride solution (2×), 5% sodium bicarbonate solution (2×) and brine. The organic layer was dried (Na$_2$SO$_4$), and concentrated in vacuo to gave a light-brown solid, which was washed with dichloromethane to afford the title compound (7.8 g, 64%) as an off-white solid. MS: [M+H]$^+$=313.2. $^1$HNMR (CDCl$_3$): δ 2.44 (s, 3H), 2.51(s, 3H), 6.31 (s, 1H), 6.95 (dd, 1H), 7.07 (d, 1H, J=8.8 Hz), 7.38 (s, 1H), 7.78 (s, 1H).

Example 1 can also be prepared by the alternate route described below.

A-1. 4-Chloro-5-methyl-pyrrolo[2,1-f][1,2,4]triazine-6-carboxylic Acid Ethyl Ester A 10 L reactor was charged with 4-hydroxy-5-methyl-pyrrolo[2,1-f][1,2,4]triazine-6-carboxylic acid ethyl ester (155.1 g, 0.70 mol) and toluene (2.7 L). Phosphorous oxychloride (128.8 g, 78 mL, 0.84 mol) was then added followed by the addition of diisopropylethylamine (94.2 g, 127 mL, 0.70 mol). The reaction mixture was stirred for 5 min at room temperature and then heated at reflux for 20 h. HPLC analysis indicated complete disappearance of starting material. The reaction mixture was then cooled to 0° C. and cold K$_2$HPO$_4$ solution (527 g in 2.4 L of water) was added at a rate to maintain the internal temperature of the reaction mixture below 5° C. The final pH of the mixture was 8. The mixture was then stirred at between 0° C. to 5° C. for 20 min and then at room temperature for 1 h. The organic phase was separated and washed with K$_2$HPO$_4$ solution (85 g in 405 mL of water) and water (345 mL) and then filtered and concentrated in vacuo until yellow solids began to precipitate. Dimethyl formamide (1 L) was added and the remaining toluene was removed in vacuo (bath temperature=38° C., pressure=9 Torr). After concentration, approximately 4% toluene was observable by HPLC.

J. 4-(4-Fluoro-2-methyl-1H-indol-5-yloxy)-5-methylpyrrolo[2,1-f][1,2,4]triazine-6-carboxylic Acid Ethyl Ester The residue from previous step A-1 was transferred to a 10 L reactor and dimethyl formamide (1.1 L) was added followed by K$_2$CO$_3$ (276 g, 2.1 mol) and 4-fluoro-2-methyl-1H-indol-5-ol (109.5 g, 0.70 mol). The reaction mixture was stirred at ambient temperature for 16 h and then cooled to 0° C. Water (2.0 L) and ethyl acetate (2 L) were added at a rate so as to maintain the internal temperature below 20° C. The phases were then separated and the aqueous phase was extracted with ethyl acetate (2 L). The combined organic extracts were then washed with water (2 L), 10% aqueous LiCl (2 L) and water (2 L). Toluene (1 L) was then added and the organic extracts were concentrated in vacuo. Additional toluene (500 mL) was added and the mixture was reconcentrated in vacuo. LC/MS; (M+H)$^+$=369.4. $^1$HNMR (CDCl$_3$): δ 1.41 (t, 3H, J=7.15 Hz), 2.45 (s, 3H), 2.87 (s, 3H), 4.39 (q, 2H, J=7.15 Hz), 6.34 (s, 1H), 6.98 (dd, 1H), 7.08 (d, 1H, J=8.25 Hz), 7.90 (s, 1H), 8.15 (s, 1H).

K. 2-[4-(4-Fluoro-2-methyl-1H-indol-5-yloxy)-5-methyl-pyrrolo[2,1-f][1,2,4]triazin-6-yl]-propan-2-ol The residue from the previous step (step J) was transferred to a 10 L reactor and enough toluene was added to provide a total reaction volume of 1.1 L. THF (1.1 L) was then added followed by the addition of LiCl (140 g) and the reaction mixture was cooled to 0° C. Methyl magnesium bromide [1.4 M in toluene, THF (75:25), 2.1 L, 2.8 mol] was then added at a rate so as to maintain an internal temperature below 5° C. Total addition time was approximately 2 h. The reaction mixture was stirred at 0° C. for an additional 2 h and then warmed to 15° C. over 3 h, at which time 5% of the starting material was still observable by HPLC. The reaction mixture was then recooled to 5° C. and an additional 100 mL of methylmagnesium bromide was added and the mixture was stirred for an additional 1.5 h. Ethyl acetate (1.5 L and a solution of 15% NH$_4$Cl (3.2 L) and) were then added so as maintain an internal temperature below 5° C. The layers were then separated and the aqueous phase was extracted with ethyl acetate (2 L). The combined organic layers were washed with 15% NH$_4$Cl (2×2 L) and water (2×2 L) and then concentrated in vacuo to afford the desired product as an amorphous yellow solid. The crude product was dissolved in dichloromethane (5 L) using a water bath (T=37° C.) to aid dissolution. The solution was then passed through a short pad of silica gel (400 g) and the pad was washed with dichloromethane (7 L) and 5% ethyl acetate/dichloromethane (1.2 L). The filtrate was evaporated to yield an off-white solid to which ethyl acetate (1.2 L) was added. The resulting slurry was transferred to a 10 L reactor and a clear solution was obtained after stirring for 2 h at 50° C. The solution was then cooled to ambient temperature and a white solid precipitated. Heptane (2.6 L) was then added and the mixture was stirred at room temperature for 20 h. The resulting solids were filtered, washed with heptane (1 L) and dried under reduced pressure at 50° C. for 24 h. 2-[4-(4-Fluoro-2-methyl-1H-indol-5-yloxy)-5-methylpyrrolo[2,1-f][1,2,4]triazin-6-yl]-propan-2-ol was obtained as a white solid (186 g, 75% over 3 steps). LC/MS; (M+H)$^+$=355.4

I-1. 4-(4-Fluoro-2-methyl-1H-indol-5-yloxy)-5-methylpyrrolo[2,1-f][1,2,4]triazin-6-ol To a solution of BF$_3$.OEt$_2$ (120 mL, 0.948 mol) in dichloromethane (200 mL) at 0° C. was added H$_2$O$_2$ (50% aqueous solution, 4.6 mL, 0.0790 mol). The reaction mixture was stirred at 0° C. for 30 min and then cooled to −20° C. In a separate flask, 2-[4-(4-fluoro-2-methyl-1H-indol-5-yloxy)-5-methylpyrrolo[2,1-f][1,2,4]triazin-6-yl]-propan-2-ol from previous step (20 g, 0.0564 mol) was dissolved in dichloromethane (400 mL) using indirect heat to achieve complete dissolution. This solution was then added rapidly via canula (addition time=20 min) to the peroxide solution. The reaction temperature during the addition was between −15° C. and −25° C. After the addition was complete, the reaction temperature was raised to −15° C. and maintained at that temperature for an additional 40 min. The reaction mixture was quenched by the addition of Na$_2$SO$_3$ (200 mL, 20% aqueous solution) and ethanolamine (33% aqueous solution, 300 mL). Both reagents were added at a rate so as to maintain the internal temperature below 0° C. The cooling bath was removed and the reaction mixture was stirred for 2 h and then poured into a separatory funnel. The layers were separated and the aqueous phase was extracted with ethyl acetate (100 mL). The combined organic layers were washed with 5% aqueous citric acid (100 mL), 10% aqueous NaHCO$_3$ (100 mL), water (2×100 mL), and brine (100 mL) and then dried, filtered and concentrated in vacuo to afford an orange foam. The crude material was loaded onto a Florisil® column using tetrahydrofuran as the loading solvent and the column was eluted with 30% ethyl acetate/heptane. The fractions containing the desired product were collected and concentrated in vacuo and then recrystallized from ethyl acetate/heptane. The solids were collected and washed with heptane to afford 9.1 g (52%) of the desired product as an off-white solid. The filtrate was concentrated in vacuo and purified on silica gel using 40% ethyl acetate/heptane as the eluent to afford and additional 2.5 g (14%) of the desired product. Total yield of 4-(4-fluoro-2-methyl-1H-indol-5-yloxy)-5-methylpyrrolo[2,1-f][1,2,4]triazin-6-ol was (11.6 g, 66%). Reverse phase HPLC: 3.75 min (YMC S5 ODS column 4.6×50 mm, 10-90% aqueous methanol over 4 minutes containing 0.2% phosphoric acid, 4 mL/min, monitoring at 220 nm). LC/MS; (M+H)$^+$=313.2

Preparation of 4-Fluoro-2-methyl-1H-indol-5-ol

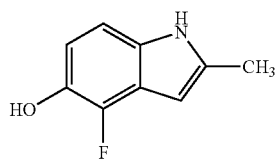

L. 1-(2,3-Difluoro-6-nitrophenyl)-propan-2-one

A 10 liter reactor was charged with potassium tert-butoxide (570.6 g, 5.082 mol) and tetrahydrofuran (2 L). Overhead stirring was initiated and the resulting suspension was cooled to 11° C. before ethyl acetoacetate (668 mL, 5.082 mol) was added. The addition of the ethyl acetoacetate required 1 h and an exotherm was observed. The rate of addition was controlled so that the internal temperature of the reactor did not exceed 25° C. The resulting mixture became homogeneous and was pale yellow in color. After addition was completed, the reaction mixture was cooled between 10° C. and 15° C. and then 1,2,3-trifluoronitrobenzene (260 mL, 600 g, 2.259 mol) was added dropwise as a solution in tetrahydrofuran (1 L). The addition required 35 min and an exotherm was observed. The rate of addition was controlled so an internal temperature of 21° C. was not exceeded. After addition was complete, the resulting brown reaction mixture was warmed to RT and stirred for 2.5 h, at which time, LC analysis indicated 100% conversion with no trace of 1,2,3-trifluoronitrobenzene remaining. The reaction mixture was recooled to 15° C. and 3 L of 1 N HCl were slowly added over 15 min and the brown solution eventually became a clear yellow solution. The pH of the aqueous phase was ~pH 4. The mixture was extracted with ethyl acetate (2×1 L) and the combined organic extracts were washed with brine (1 L) and concentrated in vacuo to afford an orange oil.

The oil obtained was charged into a 10 L reactor and dissolved in glacial acetic acid (1 L). Sulfuric acid (conc., 1 L) was then added and a vigorous evolution of gas was observed in addition to a slight exotherm. Mechanical stirring was initiated and the reaction mixture was heated at 70° C. for 3 h, after which time LC analysis indicated 100% conversion. The reaction mixture was cooled to between 15° C. to 20° C. and ethyl acetate (3 L) was added followed by the addition of water (6 L). No visible interface was observable. Seven liters of aqueous phase were separated and then extracted with ethyl acetate (2×2 L). At this time, a visible interface was observable. The combined organic extracts were washed with 1 N NaOH (6×1 L) (the pH of the aqueous phase was 6.6) and brine (3×1 L). The brown organic extracts were concentrated under reduced pressure (bath temperature 35° C., 36 torr) for ~10 h to afford 569 g of the desired compound as a crude brown oil which was 82% AP by HPLC.

Residual ethyl acetate was 3% by GC. KF: 0.25%. $^1$H and $^{13}$C NMR matched reported data. Major impurity: para regioisomer.

M. A mixture of 1-(2,3-difluoro-6-nitrophenyl)-propan-2-one (183 g) and potassium carbonate (100 g) in methanol (1 L) was heated at reflux for 3 h. The reaction mixture was then cooled and concentrated in vacuo to remove most of the methanol. The residue was diluted with ethyl acetate (1 L), filtered and washed with water. The separated aqueous layer was neutralized with 2N HCl and extracted with ethyl acetate (2×500 mL). The combined organic layer was washed with brine, dried (Na$_2$SO$_4$) and concentrated in vacuo to give a brown solid. The solid was triturated with diethyl ether and filtered to provide 1-(2-fluoro-3-methoxy-6-nitrophenyl)-propan-2-one (121 g, 71%) as a yellow solid. LC/MS; (M+H)$^+$=228.2.

N. A mixture of 1-(2-fluoro-3-methoxy-6-nitrophenyl)-propan-2-one from previous step (454 mg, 21 mmol) and pyridinium chloride (0.9 g, 7.8 mmol) was stirred at 180° C. for 75 min. The reaction was cooled to room temperature, diluted with 1N HCl (3 mL) and ethyl acetate (10 mL) and filtered. The filtrate was washed with brine (2×), dried and concentrated in vacuo to give 1-(2-fluoro-3-hydroxy-6-nitrophenyl)-propan-2-one (410 mg, 96%) as a grey solid, which was used without further purification for the next step. LC/MS; (M+H)$^+$=214. $^1$HNMR (CDCl$_3$): δ 2.37 (s, 3H), 4.22 (s, 2H), 6.95 (dd, 1H), 7.95 (d, 1H, J=9.35 Hz).

O. 1-(2-fluoro-3-hydroxy-6-nitrophenyl)-propan-2-one from previous step (50 g, 0.234 mol) was added to 2 liter round bottom flask. Water (1 L) was added, and the yellow suspension was stirred at RT. Sodium dithionite (225 g, 5.5 eq) was added in one portion and the reaction mixture was stirred and kept <30° C. until HPLC analysis indicated no starting material remained (typically less than 1 hour). Upon completion, the reaction mixture was cooled to 0° C. and the tan solid product was collected by vacuum filtration. The wet product was dried at <50° C. under house vacuum to afford 4-fluoro-2-methyl-1H-indol-5-ol (31.4 g, 81% yield) which was isolated as a tan crystalline powder. The material had an HPLC purity of >99.8. $^1$H NMR (CDCl$_3$, 400 MHz) δ 7.8 (s, 1H), 6.9-6.7 (m, 2H), 6.2 (s, 1H), 4.7 (s, 1H), 2.4 (s, 3H). $^{13}$C NMR (CDCl₃, 100 MHz) δ 145.7, 143.4, 137.5, 136.7, 134.4, 120.1, 112.7, 106.8, 95.4, 13.3.

Also, 1-(2,3-difluoro-6-nitrophenyl)-propan-2-one could be converted to the title compound by an alternate route as described below.

P. 1-(3-Benzyloxy-2-fluoro-6-nitro-phenyl)-propan-2-one

To a solution of 1-(2,3-difluoro-6-nitrophenyl)-propan-2-one (2.5 g, 82% purity by HPLC analysis, 9.54 mmol) were added benzyl alcohol (2.5 mL) and LiOH.H₂O (1.07 g, 25.58 mmol). The reaction mixture was then heated to 100-110° C. and stirred for 4 hours until HPLC analysis indicated complete reaction. After cooling to RT, the reaction mixture was diluted with dichloromethane (18 mL) and neutralized to pH 6-7 with 1 N HCl. The layers were separated and the organic phase was washed with brine and collected. With stirring, heptane (30-25 mL) was added to the organic solution whereupon crystallization was initiated. The resulting slurry was cooled to 0-5° C. and stirred for an additional 1 h. The slurry was then filtered and the filter cake was washed with heptane. The yellow-brown solids were then dried in vacuo at 50° C. for 12-15 h to afford 1.6 g of the desired compound which was 95% pure by HPLC analysis. HPLC method: Column: YMC Pack Cyano 3 um 4.6×50 mm Solvent A: 0.05% TFA in MeOH:Water (20:80), Solvent B: 0.05% TFA in MeOH:water (20:80), Wavelength: 254 nm Flow Rate: 3 mL/min. Gradient Time: 3 min. Final % B: 100 Initial Hold: 0.5 min. Start % B: 0. Typical Retention Times: SM, 1.2 min; Product 2.2-2.3 min.

Q. 4-Fluoro-2-methyl-1H-indol-5-ol

To a solution of compound P from previous step (20.00 g, 66.03.30 mmol) in methanol under a nitrogen atmosphere (300 mL) at room temperature in the absence of light were added 10% Pd/C (2.0 g) and ammonium formate (60.0 g, 0.95 mol). The reaction mixture was stirred for 3.5 h and then diluted with ethyl acetate (200 mL) and filtered through a Celite®/silica gel pad. The residue can then be purified by either of the following methods:

After concentration in vacuo, the resulting residue was purified by chromatography eluting with 30% ethyl acetate/hexanes to afford (7.32 g, 67%) of the desired compound as a white solid after trituration with dichloromethane/hexanes. After concentration in vacuo, the residue was dissolved in dichloromethane and passed through a silica gel pad washing with dichloromethane. The filtrate was concentrated in vacuo to afford (6.66 g, 61%) of the title compound as a white solid.

1-(3-Benzyloxy-2-fluoro-6-nitro-phenyl)-propan-2-one can also be converted to 1-(2-fluoro-3-hydroxy-6-nitrophenyl)-propan-2-one by the following two alternate methods.

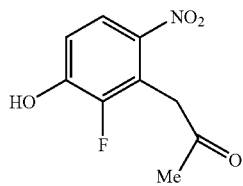

1-(2-fluoro-3-hydroxy-6-nitrophenyl)-propan-2-one

Method R-1: To a solution of 1-(3-benzyloxy-2-fluoro-6-nitrophenyl)-propan-2-one (3.03 g, 10 mmol) in acetic anhydride (5 mL) and acetic acid (5 mL) at room temperature was added hydrobromic acid (48% aqueous solution, 3 mL). After addition, the reaction was heated at 100° C. for 30 min and then cooled to room temperature. To this mixture was added 10 mL of hexanes with stirring. The solution was decanted and concentrated. The residue was diluted with ethyl acetate (50 mL) and washed with brine (3×20 mL). The organic layer was dried and concentrated in vacuo to provide 1-(2-fluoro-3-hydroxy-6-nitrophenyl)-propan-2-one (1.70 g, 80%) as a brown solid, which was used in the next step without further purification. LC/MS; (M+H)⁺=213.2

Method R-2: A mixture of 1-(3-benzyloxy-2-fluoro-6-nitrophenyl)-propan-2-one (65.0 g, 0.214 mol) and pyridinium chloride (60.74 g, 0.526 mol) was stirred at 180° C. for 1 hr. The reaction mixture was cooled to room temperature, diluted with 3N HCl (100 mL) and ethyl acetate (500 mL) and filtered. The aqueous layer was extracted with ethyl acetate (2×) and the combined organic layers were washed with brine, dried (MgSO₄),s filtered through a pad of silica gel and concentrated in vacuo. The residue was decolorized with charcoal in methanol, filtered and concentrated in vacuo to afford 1-(2-fluoro-3-hydroxy-6-nitrophenyl)-propan-2-one (37 g, 81%) as a brown solid. LC/MS; (M+H)⁺=213.2

Alternatively, 1-(3-benzyloxy-2-fluoro-6-nitrophenyl)-propan-2-one can be cyclized to 5-benzyloxy-4-fluoro-2-methyl-1H-indole as described below, which then can be debenzylated as described before.

S. A mixture of 1-(3-benzyloxy-2-fluoro-6-nitrophenyl)-propan-2-one (9.09 g, 30 mmol) and Raney nickel (~5 g) in methanol (100 mL) was heated to 40° C. and then a solution of hydrazine in methanol (15 mL) was added dropwise with vigorous stirring over a period of 30 min. After refluxing for 1 h, the reaction mixture was cooled to room temperature, filtered through Celite and concentrated. The crude material was passed through a pad of silica gel eluting with dichloromethane and concentrated in vacuo to provide 5-benzyloxy-4-fluoro-2-methyl-1H-indole (6.1 g, 80%) as a yellowish oil. LC/MS; (M+H)⁺=256.3⁺.

Example 2

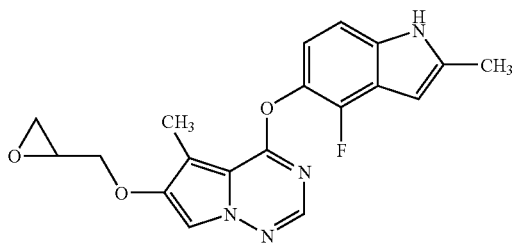

4-(4-Fluoro-2-methyl-1H-indol-5-yloxy)-5-methyl-6-oxiranylmethoxypyrrolo[2,1-f][1,2,4]triazine A mixture of 4-(4-fluoro-2-methyl-1H-indol-5-yloxy)-5-methylpyrrolo[2,1-f][1,2,4]triazin-6-ol (Example 1), (200 mg, 0.64 mmol), epichlorohydrin (297 mg, 3.21 mmol) and potassium carbonate (445 mg, 3.21 mmol) in DMF (1 ml) was stirred at 50° C. for 6 h. After cooling to RT and concentration in vacuo the crude material was purified by chromatography on silica gel eluting with 50% ethyl acetate in hexanes to afford the title compound (190 mg, 81%) as a yellowish solid. MS: (M+H)⁺=369.

Example 3

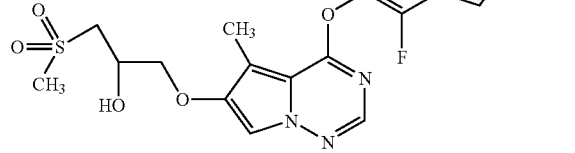

1-[4-(4-Fluoro-2-methyl-1H-indol-5-yloxy)-5-methyl-pyrrolo[2,1-f][1,2,4]triazin-6-yloxy]-3-methanesulfonyl-propan-2-ol A mixture of Example 2 (10 mg, 0.027 mmol) and sodium methanesulfinate (120 mg, 85%, 1.0 mmol) in DMSO was heated at 105° C. for 1 hr. The mixture was concentrated and purified by chromatography on silica gel eluting with 5% methanol in ethyl acetate to provide the title compound (5.5 mg, 45%) as a white solid. MS: (M+H)⁺=449.3

Example 4

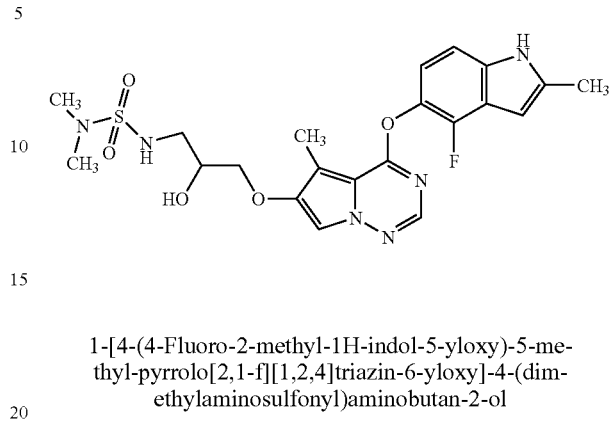

1-[4-(4-Fluoro-2-methyl-1H-indol-5-yloxy)-5-methyl-pyrrolo[2,1-f][1,2,4]triazin-6-yloxy]-4-(dimethylaminosulfonyl)aminobutan-2-ol A mixture of Example 2 (40 mg, 0.11 mmol), N,N-dimethylsulfamide (94 mg, 0.66 mmol) and potassium carbonate (91 mg, 0.66 mmol) in DMF (0.5 ml) was stirred at 80° C. for 1.5 h. The mixture was diluted with dichloromethane, filtered and concentrated in vacuo. The crude material was purified by preparative HPLC, followed by chromatography on silica gel eluting with 10% methanol in ethyl acetate to afford the title compound (13.7 mg, 25% yield) as a white solid. MS: (M+H)⁺=493.1

The following compounds were prepared using a procedure similar to that described for the preparation of Example 4 using appropriate nucleophiles shown in the table.

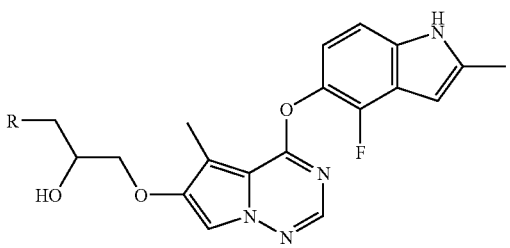

| Example # | R | | LC/MS | % yield |
|---|---|---|---|---|
| 5 | 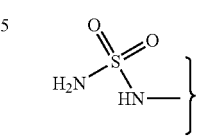 | 1-[4-(4-Fluoro-2-methyl-1H-indol-5-yloxy)-5-methy-pyrrolo[2,1-f][1,2,4]triazin-6-yloxy]-4-(aminosulfonyl)aminobutan-2-ol | 465 | 29 |
| 6 | 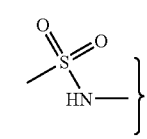 | N-{3-[4-(4-Fluoro-2-methyl-1H-indol-5-yloxy)-5-methy-pyrrolo[2,1-f][1,2,4]triazin-6-yloxy]-2-Hydroxy-propyl}-methanesulfonamide | 464 | 29 |

-continued

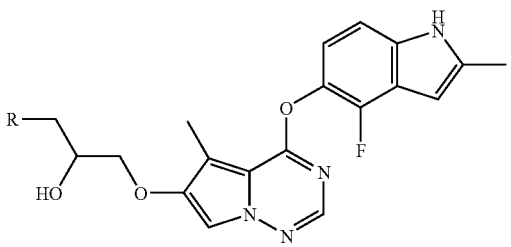

| Example # | R | | LC/MS | % yield |
|---|---|---|---|---|
| 7 | 2-ethyl-imidazol-1-yl | 1-(2-Ethyl-imidazol-1-yl)-3-[4-(4-fluoro-2-methyl-1H-indol-5-yloxy)-5-methy-pyrrolo[2,1-f][1,2,4]triazin-6-yloxy]-propan-2-ol | 465 | 33 |
| 8 | 2-methyl-imidazol-1-yl | 1-[4-(4-Fluoro-2-methyl-1H-indol-5-yloxy)-5-methy-pyrrolo[2,1-f][1,2,4]triazin-6-yloxy]-3-(2-methyl-imidazol-1-yl)-propan-2-ol | 451 | 80 |
| 9 | imidazol-1-yl | 1-[4-(4-Fluoro-2-methyl-1H-indol-5-yloxy)-5-methy-pyrrolo[2,1-f][1,2,4]triazin-6-yloxy]-3-imidazol-1-yl-propan-2-ol | 437 | 50 |
| 10 | [1,2,4]triazol-1-yl | 1-[4-(4-Fluoro-2-methyl-1H-indol-5-yloxy)-5-methy-pyrrolo[2,1-f][1,2,4]triazin-6-yloxy]-3-[1,2,4]triazol-1-yl-propan-2-ol | 438 | 45 |
| 11 | pyridin-3-yloxy | 1-[4-(4-Fluoro-2-methyl-1H-indol-5-yloxy)-5-methy-pyrrolo[2,1-f][1,2,4]triazin-6-yloxy]-3-(pyridin-3-yloxy)-propan-2-ol | 464 | 76 |
| 12 | 2-oxo-pyrrolidin-1-yl | 1-{3-[4-(4-Fluoro-2-methyl-1H-indol-5-yloxy)-5-methy-pyrrolo[2,1-f][1,2,4]triazin-6-yloxy]-2-hydroxy-propyl}-pyrrolidin-2-one | 453 | 12 |

Example 13

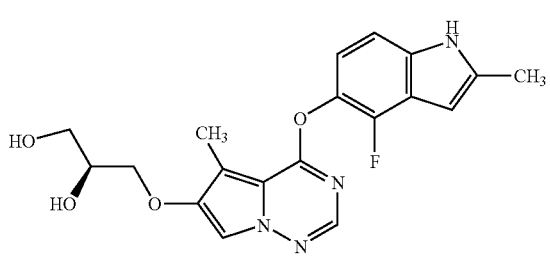

(2S)-3-[4-(4-Fluoro-2-methyl-1H-indol-5-yloxy)-5-methyl-pyrrolo[2,1-f][1,2,4]triazin-6-yloxy]-propane-1,2-diol A mixture of Example 1 (45 mg, 0.14 mmol), S-(−) glycidol (330 mg, 4.2 mmol) and triethylamine (5 μL) in ethanol (15 mL) was heated at 75° C. for 2 h. The reaction was concentrated in vacuo. The crude material was purified by chromatography on silica gel eluting with 100% ethyl acetate to provide the title compound (26 mg, 48% yield) as a white solid. MS: (M+H)$^+$=387.2

The following compounds were prepared from Example 1 using a procedure similar to that described for the preparation of Example 13 using appropriate epoxides. For examples 15 and 16, appropriate chiral propylene oxide (10 eq) was used. For examples 17 and 18, appropriate chiral glycidyl methyl ether (7 eq) was used.

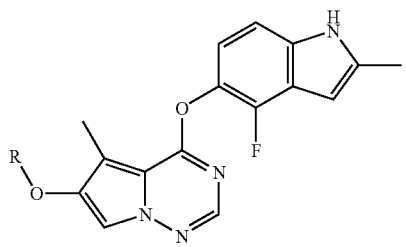

| Example # | R | Name | MS(M + H)+ | % yield |
|---|---|---|---|---|
| 14 | HO—CH₂—CH(OH)— | (2R)-3-[4-(4-Fluoro-2-methyl-1H-indol-5-yloxy)-5-methylpyrrolo[2,1-f][1,2,4]triazin-6-yloxy]-propane-1,2-diol | 387 | 33 |
| 15 | (R)-CH(OH)CH₃ | (2R)-1-[4-(4-Fluoro-2-methyl-1H-indol-5-yloxy)-5-methylpyrrolo[2,1-f][1,2,4]triazin-6-yloxy]-propan-2-ol | 371 | 82 |
| 16 | (S)-CH(OH)CH₃ | (2S)-1-[4-(4-Fluoro-2-methyl-1H-indol-5-yloxy)-5-methylpyrrolo[2,1-f][1,2,4]triazin-6-yloxy]-propan-2-ol | 371 | 54 |
| 17 | Me-O-CH₂-CH(OH)- (R) | (2R)1-[4-(4-Fluoro-2-methyl-1H-indol-5-yloxy)-5-methylpyrrolo[2,1-f][1,2,4]triazin-6-yloxy]-3-methoxy-propan-2-ol | 401 | 47 |
| 18 | Me-O-CH₂-CH(OH)- (S) | (2S)-1-[4-(4-Fluoro-2-methyl-1H-indol-5-yloxy)-5-methylpyrrolo[2,1-f][1,2,4]triazin-6-yloxy]-3-methoxy-propan-2-ol | 401 | 46 |

Elemental Analysis for Example 14: Calc for $C_{19}H_{19}FN_4O_4$, C 59.06%, H 4.95%, N 14.50%, found; C 58.96%, H 4.96%, N 14.43%. HRMS; (M+H)+: 387.1455

Elemental Analysis for Example 15: Calc for $C_{19}H_{19}FN_4O_3$, C 61.61%, H 5.17%, N 15.12%, F 5.13%, found; C 61.35%, H 5.06%, N 14.99%, F 4.88%. HRMS; (M+H)+: 371.1522.

Elemental Analysis for Example 17: Calc. for $C_{20}H_{21}FN_4O_4$, C 59.99%, H 5.28%, N 13.99%, found; C 60.19%, H 5.12%, N 13.91%. HRMS (M+H)+: 401.1638

Elemental Analysis for Example 18: Calc. for $C_{20}H_{21}FN_4O_4$, C 59.99%, H 5.28%, N 13.99%, found; C 59.98%, H 5.23%, N 13.88%. HRMS (M+H)$^+$: 401.1621

Example 19

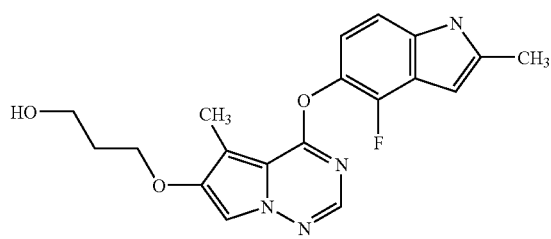

3-[4-(4-Fluoro-2-methyl-1H-indol-5-yloxy)-5-methyl-pyrrolo[2,1-f][1,2,4]triazin-6-yloxy]-propan-1-ol A mixture of Example 1 (50 mg, 0.16 mmol), 3-bromo-1-propanol (100 μL, 1.1 mmol) and potassium carbonate (100 mg, 0.72 mmol) in acetonitrile (1.5 mL) was stirred overnight at 35° C. The mixture was filtered, concentrated and purified by chromatography on silica gel eluting with 30% ethyl acetate in dichloromethane to provide the title compound (26 mg, 39% yield) as a light beige solid. MS: (M+H)$^+$=371

Example 20

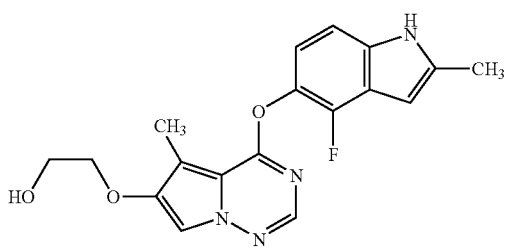

2-[4-(4-Fluoro-2-methyl-1H-indol-5-yloxy)-5-methylpyrrolo[2,1-f][1,2,4]triazin-6-yloxy]-ethanol Example 1 was treated with bromoethanol (13 eq.) in a manner similar to the preparation of Example 19 to obtain the title compound (49%). LC/MS; (M+H)$^+$=357.

Example 21

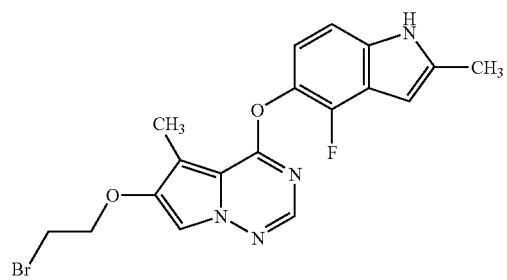

6-(2-Bromoethoxy)-4-(4-fluoro-2-methyl-1H-indol-5-yloxy)-5-methylpyrrolo[2,1-f][1,2,4]triazine A mixture of Example 1 (300 mg, 0.96 mmol), 1,2-dibromoethane (1.5 mL, 17.4 mmol), and potassium carbonate (1.0 g, 7.2 mmol) in acetonitrile (10 mL) was heated at 50° C. for 6 h. The mixture was diluted with dichloromethane, filtered and concentrated in vacuo. The crude material was purified by chromatography on silica gel eluting with 10% ethyl acetate in dichloromethane to provide the title compound (405 mg, 100%) as a white solid. MS: (M+H)$^+$=419.

The following compounds were prepared using a procedure similar to that described for the preparation of Example 21 using appropriate bromides.

| Example # | R | Name | LC/MS; (M + H)$^+$ | % yield |
|---|---|---|---|---|
| 22 | 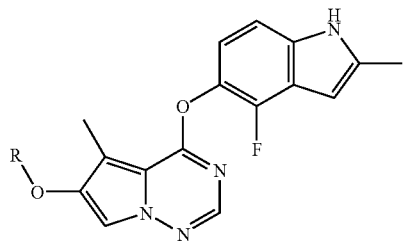 | 6-(3,3-Dimethoxy-propoxy)-4-(4-fluoro-2-methyl-1H-indol-5-yloxy)-5-methylpyrrolo[2,1-f][1,2,4]triazine | 415 | 81 |

-continued

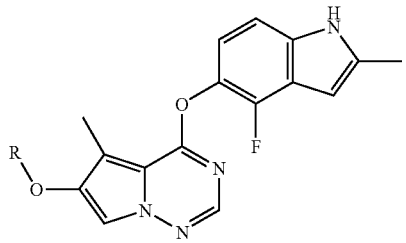

| Example # | R | Name | LC/MS; (M + H)+ | % yield |
|---|---|---|---|---|
| 23 | (methanesulfonyl-propan-2-one group) | 1-[4-(4-Fluoro-2-methyl-1H-indol-5-yloxy)-5-methyl-pyrrolo[2,1-f][1,2,4]triazin-6-yloxy]-3-methanesulfonyl-propan-2-one | 447.4 | 10 |

Example 24

N-{2-[4-(4-Fluoro-2-methyl-1H-indol-5-yloxy)-5-methyl-pyrrolo[2,1-f][1,2,4]triazin-6-yloxy]}-(dimethylaminosulfonyl)ethylamine

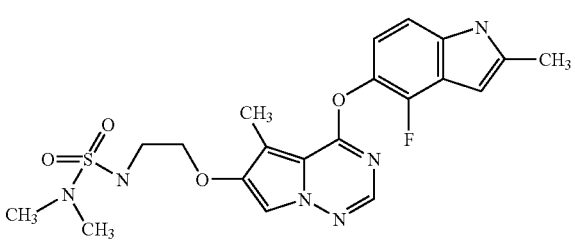

A mixture of Example 21 (80 mg, 0.19 mmol), N,N-dimethylsulfamide (150 mg, 1.2 mmol) and potassium carbonate (400 mg, 2.9 mmol) in DMF (1.5 mL) under argon was stirred at 80° C. for 2 h. The reaction mixture was cooled to RT, diluted with $CH_2Cl_2$, filtered and concentrated. The crude material was purified by preparative HPLC to afford the title compound (48 mg, 55% yield) as a white solid. MS: $(M+H)^+$= 463.2

The following compounds were prepared using a procedure similar to that described for the preparation of Example 24 using appropriate nucleophiles. Formylurea was used for the preparation of Example 27.

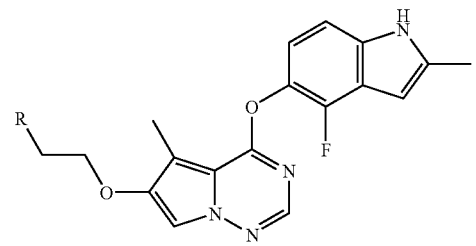

| Example # | R | Name | LC/MS; (M + H)+ | % yield |
|---|---|---|---|---|
| 25 | H2N-S(O)(O)-NH- | N-{2-[4-(4-Fluoro-2-methyl-1H-indol-5-yloxy)-5-methyl-pyrrolo[2,1-f][1,2,4]triazin-6-yloxy]}-(aminosulfonyl)ethylamine | 435 | 31 |
| 26 | Me-S(O)(O)-NH- | N-{2-[4-(4-Fluoro-2-methyl-1H-indol-5-yloxy)-5-methyl-pyrrolo[2,1-f][1,2,4]triazin-6-yloxy]-ethyl}-methanesulfonamide | 434 | 67 |

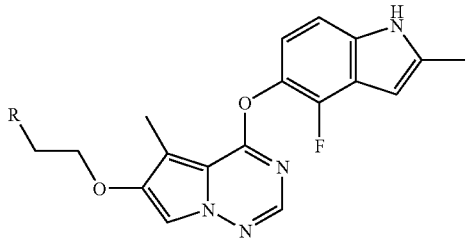

| Example # | R | Name | LC/MS; (M + H)+ | % yield |
|---|---|---|---|---|
| 27 | H-N(H)-C(=O)- (via ethyl linker) | N-{2-[4-(4-Fluoro-2-methyl-1H-indol-5-yloxy)-5-methyl-pyrrolo[2,1-f][1,2,4]triazin-6-yloxy]-ethyl}-formamide | 384 | 75 |

Example 28

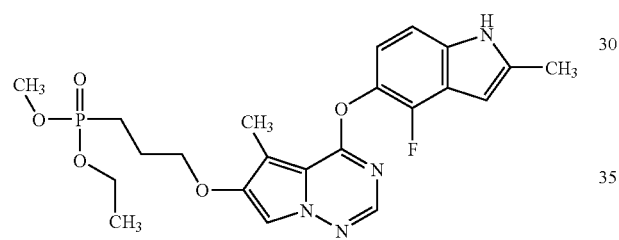

{3-[4-(4-Fluoro-2-methyl-1H-indol-5-yloxy)-5-methyl-pyrrolo[2,1-f][1,2,4]triazin-6-yloxy]-propyl}-phosphonic Acid Diethyl Ester A. 6-(3-Bromo-propoxy)-4-(4-fluoro-2-methyl-1H-indol-5-yloxy)-5-methylpyrrolo[2,1-f][1,2,4]triazine To a solution of Example 1 (40 mg, 0.13 mmol), 3-bromo-1-propanol (36 mg, 0.26 mmol) and triphenylphosphine (68 mg, 0.26 mmol) under argon at 0° C. was added DEAD (45 mg, 0.26 mmol). The mixture was stirred at room temperature for 3 h and concentrated in vacuo. The residue was purified by chromatography on silica gel eluting with 20% ethyl acetate in dichloromethane to obtain compound A (37 mg, 66%) as a white solid. LC/MS; (M+H)+=433

B. {3-[4-(4-Fluoro-2-methyl-1H-indol-5-yloxy)-5-methylpyrrolo[2,1-f][1,2,4]triazin-6-yloxy]-propyl}-phosphonic Acid Diethyl Ester A solution of Compound A (8 mg, 0.018 mmol) in triethyl phosphite (0.5 ml) was heated at 110° C. overnight. The crude material was purified by chromatography on silica gel eluting with ethyl acetate and 10% methanol in ethyl acetate to afford the title compound (7 mg, 79%) as a clear oil. MS: (M+H)+=491

Example 29

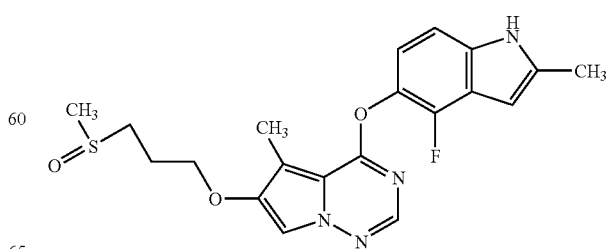

4-(4-Fluoro-2-methyl-1H-indol-5-yloxy)-5-methyl-6-(3-methylsulfanyl-propoxy)-pyrrolo[2,1-f][1,2,4]triazine The title compound was prepared (32%) using a procedure similar to that described for the preparation of step A of Example 28 except using 3-methylthio-1-propanol as the alcohol. LC/MS; (M+H)+=400

Example 30

4-(4-Fluoro-2-methyl-1H-indol-5-yloxy)-6-(3-methanesulfinyl-propoxy)-5-methylpyrrolo[2,1-f][1,2,4]triazine To a solution of Example 29 (25 mg, 0.0625 mmol) in dichloromethane at 0° C. was added m-CPBA (77%, 14 mg, 0.0625 mmol). After stirring the mixture at 0° C. for 30 min, triphenylphosphine (5 mg, 0.019 mmol) was added. After stirring at 0° C. for additional 30 min, the reaction mixture was concentrated in vacuo. The crude material was purified by preparative HPLC to afford the title compound (11 mg, 42% yield) as a white solid. MS: (M+H)$^+$=417.

Example 31

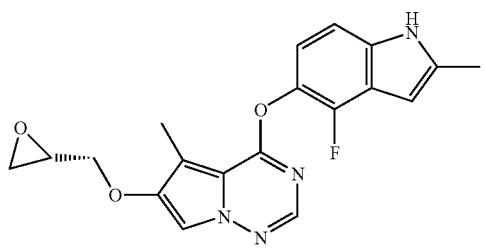

(2S)-4-(4-Fluoro-2-methyl-1H-indol-5-yloxy)-5-methyl-6-oxiranylmethoxy-pyrrolo[2,1-f][1,2,4]triazine A mixture of Example 1 (311 mg, 1 mmol), (2-(+)-glycidyl nosylate (311 mg, 1.2 mmol), and K$_2$CO$_3$ (200 mg, 1.45 mmol) in DMF (3 mL) was stirred at RT for 4 hr. The mixture was diluted with ethyl acetate and the solids were filtered. The filtrate was washed with brine, dried, and concentrated. The residue was purified by flash column chromatography (silica gel, 50% ethyl acetate in hexanes) to afford the title compound (340 mg, 92% yield). LC/MS; (M+H)$^+$=369.1

Example 32

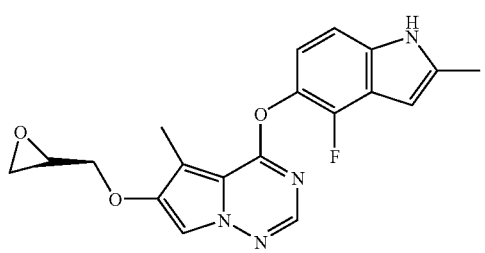

(2R)-4-(4-Fluoro-2-methyl-1H-indol-5-yloxy)-5-methyl-6-oxiranylmethoxy-pyrrolo[2,1-f][1,2,4]triazine The title compound was obtained by treating Example 1 with (2R)-(−)-glycidyl nosylate in a manner similar to the preparation of Example 31. LC/MS; (M+H)$^+$=369.2

Example 33

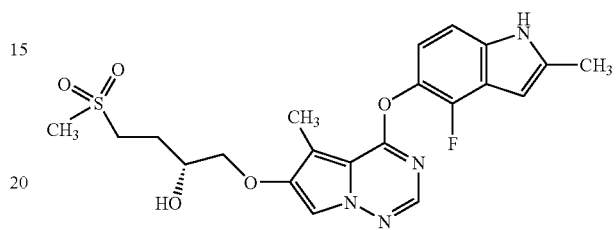

(2R)-1-[4-(4-Fluoro-2-methyl-1H-indol-5-yloxy)-5-methyl-pyrrolo[2,1-f][1,2,4]triazin-6-yloxy]-4-methanesulfonyl-butan-2-ol To a solution of dimethyl sulfone (282 mg, 3 mmol) in THF (2 mL) under argon at −78° C. was added n-butyl lithium (1.6 M in hexanes, 1.12 mmol). The reaction was stirred at −78° C. for 10 min and Example 32 (30 mg, 0.08 mmol) was added. The resulting mixture was allowed to stir at 0° C. for 30 min, diluted with dichloromethane and washed with 1% NaH$_2$PO$_4$ solution. The crude material was purified by preparative HPLC to afford the title compound (20 mg, 53%) as a white solid. MS: (M+H)$^+$=463.2

Example 34

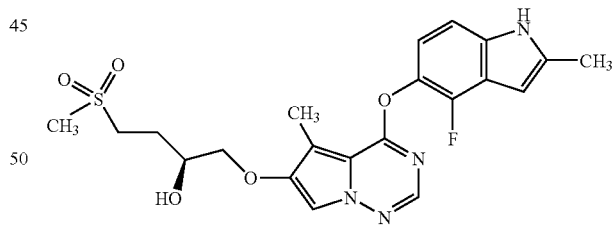

(2S)-1-[4-(4-Fluoro-2-methyl-1H-indol-5-yloxy)-5-methyl-pyrrolo[2,1-f][1,2,4]triazin-6-yloxy]-4-methanesulfonyl-butan-2-ol Example 31 was converted to the title compound using the procedure described for the preparation of Example 33 (40%). LC/MS; (M+H)$^+$=463.2

The following examples were prepared by treating appropriate chiral epoxides, Example 31 and Example 32, with triazoles using a procedure similar to the described for the conversion of Example 2 to Example 4.

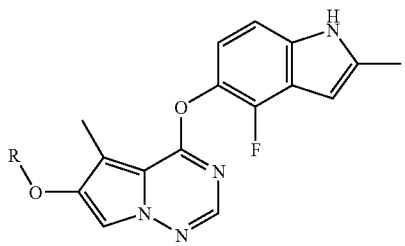

| Example # | R | Name | LC/MS; (M + H)+ | % yield |
|---|---|---|---|---|
| 35 | (1,2,4-triazol-1-yl)-CH2-CH(OH)-CH2-CH3, (2S) | (2S)-1-[4-(4-Fluoro-2-methyl-1H-indol-5-yloxy)-5-methylpyrrolo[2,1-f][1,2,4]triazin-6-yloxy]-3-[1,2,4]triazol-1-yl-propan-2-ol | 438.2 | 17 |
| 36 | (1,2,4-triazol-4-yl)-CH2-CH(OH)-CH2-CH3, (2S) | (2S)-1-[4-(4-Fluoro-2-methyl-1H-indol-5-yloxy)-5-methylpyrrolo[2,1-f][1,2,4]triazin-6-yloxy]-3-[1,2,4]triazol-4-yl-propan-2-ol | 438.1 | 6.7 |
| 37 | (1,2,3-triazol-1-yl)-CH2-CH(OH)-CH2-CH3, (2S) | (2S)-1-[4-(4-Fluoro-2-methyl-1H-indol-5-yloxy)-5-methylpyrrolo[2,1-f][1,2,4]triazin-6-yloxy]-3-[1,2,3]triazol-1-yl-propan-2-ol | 438.2 | 39 |
| 38 | (1,2,3-triazol-2-yl)-CH2-CH(OH)-CH2-CH3, (2S) | (2S)-1-[4-(4-Fluoro-2-methyl-1H-indol-5-yloxy)-5-methylpyrrolo[2,1-f][1,2,4]triazin-6-yloxy]-3-[1,2,3]triazol-2-yl-propan-2-ol | 438.1 | 30 |
| 39 | (1,2,4-triazol-4-yl)-CH2-CH(OH)-CH2-CH3, (2R) | (2R)-1-[4-(4-Fluoro-2-methyl-1H-indol-5-yloxy)-5-methylpyrrolo[2,1-f][1,2,4]triazin-6-yloxy]-3-[1,2,4]triazol-4-yl-propan-2-ol | 438.3 | 8 |
| 40 | (1,2,4-triazol-1-yl)-CH2-CH(OH)-CH2-CH3, (2R) | (2R)-1-[4-(4-Fluoro-2-methyl-1H-indol-5-yloxy)-5-methylpyrrolo[2,1-f][1,2,4]triazin-6-yloxy]-3-[1,2,4]triazol-1-yl-propan-2-ol | 438.2 | 34 |

-continued

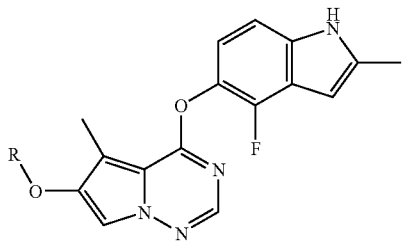

| Example # | R | Name | LC/MS; (M + H)+ | % yield |
|---|---|---|---|---|
| 41 | [triazole-CH2-CH(OH)-CH2-] | (2R)-1-[4-(4-Fluoro-2-methyl-1H-indol-5-yloxy)-5-methylpyrrolo[2,1-f][1,2,4]triazin-6-yloxy]-3-[1,2,3]triazol-1-yl-propan-2-ol | 438.2 | 24 |
| 42 | [pyrazole/triazole-CH2-CH(OH)-CH2-] | (2R)-1-[4-(4-Fluoro-2-methyl-1H-indol-5-yloxy)-5-methylpyrrolo[2,1-f][1,2,4]triazin-6-yloxy]-3-[1,2,3]triazol-2-yl-propan-2-ol | 438.1 | 24 |

Example 43

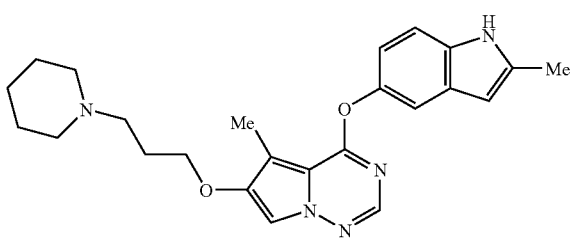

5-Methyl-4-(2-methyl-1H-indol-5-yloxy)-6-(3-piperidin-1-ylpropoxy)-pyrrolo[2,1-f][1,2,4]triazine A. 5-Methyl-4-phenoxy-6-(3-piperidin-1-yl-propoxy)-pyrrolo[2,1-f][1,2,4]triazine To a mixture of 5-methyl-4-phenoxypyrrolo[2,1-f][1,2,4]triazin-6-ol (1.47 g, 6.1 mmol, for preparation see WO 0071129), 1-piperidinepropanol (1.74 g, 12.2 mmol) and triphenylphosphine (3.2 g, 12.2 mmol) in tetrahydrofuran (20 mL) at 0° C. under argon, was added DEAD (1.9 mL, 12.2 mmol). The resulting mixture was stirred at 0° C. for 30 min, and then at RT for 1 hr. The volatiles were removed in vacuo. The residue was purified by silica gel flash column chromatography using 5% (2M NH$_3$ in MeOH)/20% ethyl acetate/CH$_2$Cl$_2$ to afford the desired product as beige solid (1.6 g, 72% yield). MS: (M+H)$^+$=367.

B. 5-Methyl-4-hydroxy-6-(3-piperidin-1-yl-propoxy)-pyrrolo[2,1-f][1,2,4]triazine A mixture of above compound A compound (1.7 g, 5.05 mmol) in aq.HCl (1N, 15 mmol) was heated at 70° C. for 3 h. The solvent was removed in vacuo. The product was purified by flash column chromatography [silica gel, 2M NH$_3$ in MeOH/EtOAc=2/8 (v/v)] to afford 5-methyl-4-phenoxy-6-(3-piperidin-1-yl-propoxy)-pyrrolo[2,1-f][1,2,4] (1.1 g, 75% yield) triazine as a white solid. MS: (M+H)$^+$=291.

C. 4-Chloro-5-methyl-6-(3-piperidin-1-yl-propoxy)-pyrrolo[2,1-f][1,2,4]triazine

A solution of compound B (0.45 g, 1.55 mmol) in POCl$_3$ (8 mL) was stirred at 80° C. for 5 h. The volatiles were removed in vacuo. The residue was dissolved in dichloromethane and the solution was washed sequentially with ice cold NaHCO$_3$ solution and brine, dried, and filtered. The filtrate was concentrated to afford 4-chloro-5-methyl-6-(3-piperidin-1-yl-propoxy)-pyrrolo[2,1-f][1,2,4]triazine (0.47 g, 98% yield) as a yellow solid. LC/MS; (M+H)$^+$=309.

D. 5-Methyl-4-(2-methyl-1H-indol-5-yloxy)-6-(3-piperidin-1-ylpropoxy)-pyrrolo[2,1-f][1,2,4]triazine A mixture of compound C (40 mg, 0.13 mmol), 2-methyl-5-hydroxyindole (40 mg, 0.27 mmol) and K$_2$CO$_3$ (100 mg, 0.72 mmol) in DMF (1 mL) was heated at 80° C. for 2 h. The solid was filtered, washed with CH$_2$Cl$_2$ and the filtrate was concentrated. The residue was purified by flash column chromatography [silica gel, 20% NH$_3$ (2M in MeOH)/ethyl acetate] to afford the title compound (24 mg, 44% yield) as a yellow solid. LC/MS; (M+H)$^+$=420.2

The following compounds were prepared using a procedure similar to that described for the preparation of Example 43 using the appropriate hydroxyindole or aminoindole.

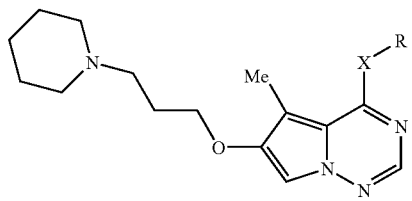

| Example # | X—R | Name | LC/MS; (M + H)+ | % yield |
|---|---|---|---|---|
| 44 | (indol-5-yloxy) | 4-(1H-Indol-5-yloxy)-5-methyl-6-(3-piperidin-1-yl-propoxy)-pyrrolo[2,1-f][1,2,4]triazine | 406 | 30 |
| 45 | (4-fluoro-indol-5-yloxy) | 4-(4-Fluoro-1H-indol-5-yloxy)-5-methyl-6-(3-piperidin-1-yl-propoxy)-pyrrolo[2,1-f][1,2,4]triazine | 424 | 26 |
| 46 | (4-fluoro-2-methyl-indol-5-yloxy) | 4-(4-Fluoro-2-methyl-1H-indol-5-yloxy)-5-methyl-6-(3-piperidin-1-yl-propoxy)-pyrrolo[2,1-f][1,2,4]triazine | 438 | 25 |
| 47 | (6-fluoro-indol-5-yloxy) | 4-(6-Fluoro-1H-indol-5-yloxy)-5-methyl-6-(3-piperidin-1-yl-propoxy)-pyrrolo[2,1-f][1,2,4]triazine | 438 | 33 |
| 48 | (indol-5-yl)amino | (1H-Indol-5-yl)-[5-methyl-6-(3-piperidin-1-yl-propoxy)-pyrrolo[2,1-f][1,2,4]triazin-4-yl]-amine | 405 | 21 |
| 49 | (2-methyl-indol-5-yl)amino | (2-Methyl-1H-indol-5-yl)-[5-methyl-6-(3-piperidin-1-yl-propoxy)-pyrrolo[2,1-f][1,2,4]triazin-4-yl]-amine | 419 | 34 |
| 50 | (2,3-dimethyl-indol-5-yl)amino | (2,3-Dimethyl-1H-indol-5-yl)-[5-methyl-6-(3-piperidin-1-yl-propoxy)-pyrrolo[2,1-f][1,2,4]triazin-4-yl]-amine | 433 | 27 |

Example 51

4-(4-Fluoro-2-methyl-1H-indol-5-yloxy)-5-methyl-6-(2-piperidin-4-yl-ethoxy)-pyrrolo[2,1-f][1,2,4]triazine

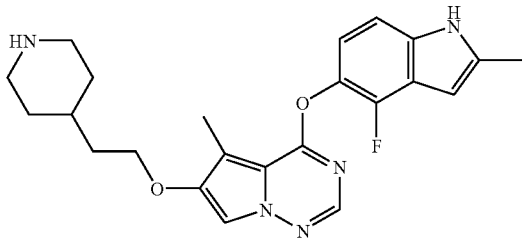

To a solution of triphenylphosphine (168 mg, 0.640 mmol) in THF (1.5 mL) at 0° C. was slowly added DEAD (76 μL, 0.48 mmol). After stirring for 5 minutes, 4-piperidineethanol (0.48 mmol) was added and the resulting mixture was stirred for an additional 5 minutes. Example 1 was then added and the reaction mixture slowly warmed to room temperature and stirred for 18 h. The reaction mixture was then concentrated in vacuo and purified by preparative HPLC followed by flash column chromatography. Aqueous 1 N HCl was added and the mixture was concentrated in vacuo to afford (30 mg, 74%) of a pinkish solid. MS: $(M+H)^+=424.23$ The following Examples were prepared using a procedure similar to that described for the preparation of Example 51 by treating Example 1 with an appropriate alcohol.

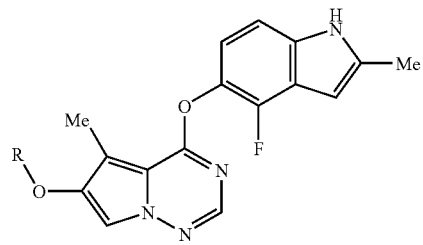

| Example # | R | Name | % Yield | LC/MS; $(M+H)^+$ |
|---|---|---|---|---|
| 52 | | 4-(4-Fluoro-2-methyl-1H-indol-5-yloxy)-5-methyl-6-(2-morpholin-4-yl-ethoxy)-pyrrolo[2,1-f][1,2,4]triazine | 71 | 426.3 |
| 53 | | {3-[4-(4-Fluoro-2-methyl-1H-indol-5-yloxy)-5-methylpyrrolo[2,1-f][1,2,4]triazin-6-yloxy]-propyl}-dimethylamine | 34 | 398.2 |
| 54 | | 4-(4-Fluoro-2-methyl-1H-indol-5-yloxy)-5-methyl-6-[2-(4-methyl-thiazol-5-yl)-ethoxy]-pyrrolo[2,1f][1,2,4]triazine | 48 | 438.2 |
| 55 | | 4-(4-Fluoro-2-methyl-1H-indol-5-yloxy)-5-methyl-6-(2-methylsulfanyl-ethoxy)-pyrrolo[2,1-f][1,2,4]triazine | 43 | 387.2 |
| 56 | | {2-[4-(4-Fluoro-2-methyl-1H-indol-5-yloxy)-5-methyl-pyrrolo[2,1-f][1,2,4]triazin-6-yloxy]-ethyl}-methylamine | 66 | 370.2 |
| 57 | | 1-{2-[4-(4-Fluoro-2-methyl-1H-indol-5-yloxy)-5-methyl-pyrrolo[2,1-f][1,2,4]triazin-6-yloxy]-ethyl}-pyrrolidin-2-one | 42 | 424.13 |

-continued

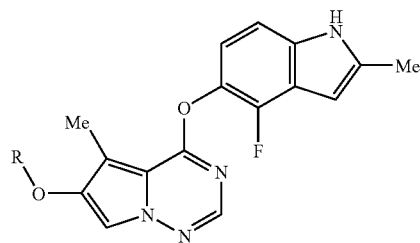

| Example # | R | Name | % Yield | LC/MS; (M + H)+ |
|---|---|---|---|---|
| 58 | (4-oxopentyl group) | 5-[4-(4-Fluoro-2-methyl-1H-indol-5-yloxy)-5-methylpyrrolo[2,1-f][1,2,4]triazin-6-yloxy]-pentan-2-one | 13 | 397.3.0 |
| 59 | (2-[1-(2-methanesulfonyl-ethyl)-piperidin-4-yl]-ethyl group) | 4-(4-Fluoro-2-methyl-1H-indol-5-yloxy)-6-{2-[1-(2-methanesulfonyl-ethyl)-piperidin-4-yl]-ethoxy}-5-methylpyrrolo[2,1-f][1,2,4]triazine | 13 | 530.0 |
| 61 | (3-(6-methylpyridin-2-yl)propyl group) | 4-(4-Fluoro-2-methyl-1H-indol-5-yloxy)-5-methyl-6-[3-(6-methyl-pyridin-2-yl)-propoxy]-pyrrolo[2,1-f][1,2,4]triazine | 28 | 446.2 |
| 62 | (3-(pyridin-4-yl)propyl group) | 4-(4-Fluoro-2-methyl-1H-indol-5-yloxy)-5-methyl-6-(3-pyridin-4-yl-propoxy)-pyrrolo[2,1-f][1,2,4]triazine | 33 | 432.2 |
| 63 | (3-(1,1-dioxothiomorpholin-4-yl)propyl group) | 6-[3-(1,1-Dioxo-1λ6-thiomorpholin-4-yl)-propoxy]-4-(4-fluoro-2-methyl-1H-indol-5-yloxy)-5-methylpyrrolo[2,1-f][1,2,4]triazine | 45 | 488.2 |
| 64 | (Cbz-NH, methanesulfonyl propyl group) | {1-[4-(4-Fluoro-2-methyl-1H-indol-5-yloxy)-5-methylpyrrolo[2,1-f][1,2,4]triazin-6-yloxymethyl]-3-methanesulfonylpropyl}-carbamic acid benzyl ester | 41 | 596.3 |
| 65 | (2-(thiophen-2-yl)ethyl group) | 4-(4-Fluoro-2-methyl-1H-indol-5-yloxy)-5-methyl-6-(2-thiophen-2-yl-ethoxy)-pyrrolo[2,1-f][1,2,4]triazine | 50 | 423.2 |
| 66 | (3-oxobutyl group) | 1-[4-(4-Fluoro-2-methyl-1H-indol-5-yloxy)-5-methyl-pyrrolo[2,1-f][1,2,4]triazin-6-yloxy]-butan-2-one | 8 | 383.2 |
| 67 | (2-methoxyethoxyethyl group) | 4-(4-Fluoro-2-methyl-1H-indol-5-yloxy)-6-[2-(2-methoxyethoxy)-ethoxy]-5-methyl-pyrrolo[2,1-f][1,2,4]triazine | 13 | 415.3 |

-continued

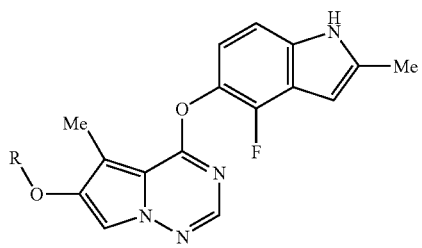

| Example # | R | Name | % Yield | LC/MS; (M + H)+ |
|---|---|---|---|---|
| 68 | cyclopropylmethyl | 6-Cyclopropylmethoxy-4-(4-fluoro-2-methyl-1H-indol-5-yloxy)-5-methylpyrrolo[2,1-f][1,2,4]triazine | 68 | 376.2 |
| 69 | 2-fluoroethyl | 6-(2-Fluoro-ethoxy)-4-(4-fluoro-2-methyl-1H-indol-5-yloxy)-5-methylpyrrolo[2,1-f][1,2,4]triazine | 8 | 359.2 |
| 70 | 2-(1,1-dioxo-thiomorpholin-4-yl)ethyl | 6-[2-(1,1-Dioxo-1λ6-thiomorpholin-4-yl)-ethoxy]-4-(4-fluoro-2-methyl-1H-indol-5-yloxy)-5-methylpyrrolo[2,1-f][1,2,4]triazine | 51 | 474.2 |

Example 71

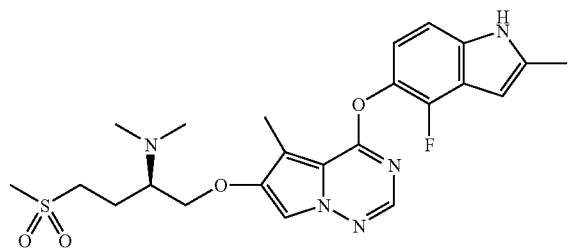

{1-[4-(4-Fluoro-2-methyl-1H-indol-5-yloxy)-5-methyl-pyrrolo[2,1-f][1,2,4]triazin-6-yloxymethyl]-3-methanesulfonyl-propyl}-dimethyl-amine Step A To a solution of Example 64 (20 mg, 0.0336 mmol) in a mixture of DMF/THF (1:1, 1 mL) at 0° C. was added NaH (1 mg, 0.0336 mmol) and the resulting mixture was stirred for 20 min. Methyl iodide (0.2 mL, excess) was then added and the reaction mixture stirred for an additional 30 min, poured onto a mixture of water (20 mL) and dichloromethane (20 mL), and the layers were separated. The aqueous phase was extracted with dichloromethane (10 mL) and the combined organic layers were dried over $Na_2SO_4$, filtered, concentrated in vacuo and used without further purification in the next step.

Step B To the material obtained in the previous step in DMF (1 mL) were added $NH_4CO_2H$ (21 mg, 0.336 mmol) and 5% Pd/C (3 mg) and the reaction mixture stirred at room temperature for 24 hours. Additional $NH_4CO_2H$ (21 mg) and Pd/C (5 mg) were added, the reaction mixture heated to 70° C. for 15 minutes and then room temperature for 14 hours. The reaction mixture was then filtered through Celite®, rinsing with dichloromethane (50 mL). The filtrate was washed with water (20 mL), dried over $Na_2SO_4$, filtered and concentrated in vacuo. The residue was purified by preparative HPLC, taken up in dichloromethane (20 mL) and washed with $NaHCO_3$ (20 mL) and concentrated in vacuo to afford the title compound (3.5 mg, 21% over 2 steps). MS: $(M+H)^+=490$.

The intermediates required for the preparation of Example 64 were prepared as follows.

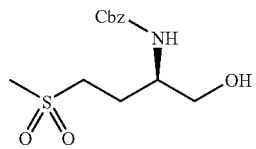

(1-Hydroxymethyl-3-methanesulfonyl-propyl)-carbamic Acid Benzyl Ester

To a solution of Cbz-L-methionine methyl ester (500 mg, 1.68 mmol) in MeOH (12 mL) at 0° C. was added Oxone (1.53 g, 5.044 mmol) in water (8 mL). The ice bath was removed and the reaction mixture was stirred for 1 h, concentrated in vacuo to remove the volatile materials and then the residue poured onto dichloromethane (50 mL) and water (50 mL). The layers were separated and the aqueous phase was extracted with dichloromethane (2×40 mL) and the combined organic extracts were washed with water (40 mL), dried over MgSO₄, filtered and concentrated in vacuo to afford 612 mg of product (>100% yield) which was used without further purification.

To a solution of the material obtained in the previous step (350 mg) in dichloromethane (6 mL) at −78° C. was added DIBAL (1.0 M hexanes, 2.33 mL, 2.33 mmol) and the reaction mixture was stirred for 1 h and then quenched at low temperature with Rochelle's salt (sat. aq., 10 mL) and stirred for an additional 1 h at room temperature. The reaction mixture was poured into a separatory funnel and the layers were separated. The aqueous phase was extracted with dichloromethane (2×25 mL) and the combined organic extracts were dried over Na₂SO₄, filtered and concentrated in vacuo to afford a mixture of aldehyde and alcohol as a white solid. This material was resubjected to the reaction conditions by dissolving the solid in dichloromethane (6 mL), cooling to −78° C. and adding DIBAL-H (1.0 M in hexanes, 1.59 mL, 1.41 mmol). The reaction mixture was slowly warmed to 0° C. over 2 h before being quenched with Rochelle's salt (sat. aq., 10 mL) and stirring for an additional 1 h at room temperature. The layers were separated, the aqueous phase was extracted with dichloromethane (2×25 mL) and the combined organic extracts were dried over Na₂SO₄, filtered and concentrated in vacuo. The residue was then triturated with a 1:2 mixture of dichloromethane:hexane to afford (1-hydroxymethyl-3-methanesulfonyl-propyl)-carbamic acid benzyl ester (118 mg, 42% yield) as a white solid.

Example 72

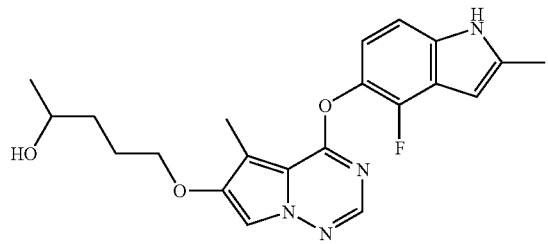

5-[4-(4-Fluoro-2-methyl-1H-indol-5-yloxy)-5-methylpyrrolo[2,1-f][1,2,4]triazin-6-yloxy]-pentan-2-ol To a solution of Example 58 (16 mg, 0.0404 mmol) in THF (1 mL) and MeOH (0.1 mL) at 0° C. was added NaBH₄ (3 mg, 0.0808 mmol) and the reaction mixture was stirred for 30 min. An additional 5 mg of NaBH₄ was added and the mixture continued to stir for 2 h at 10° C. and then 2 h at room temperature. The reaction mixture was then poured onto NaHCO₃ (20 mL) and dichloromethane (30 mL). The layers were separated and the organic phase was dried, filtered and concentrated in vacuo. The residue was absorbed onto silica and purified by flash column chromatography (50% ethyl acetate/hexane to 100% ethyl acetate) to afford the title compound (10 mg, 63% yield) MS: (M+H)⁺=399.5

Example 73

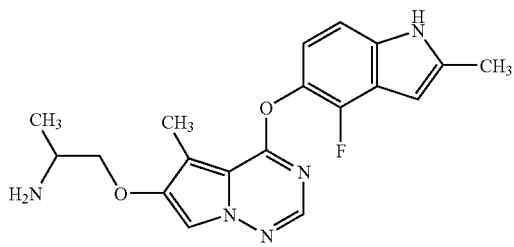

2-[4-(4-Fluoro-2-methyl-1H-indol-5-yloxy)-5-methylpyrrolo[2,1-f][1,2,4]triazin-6-yloxy]-1-methylethylamine A. 1-[4-(4-Fluoro-2-methyl-1H-indol-5-yloxy)-5-methylpyrrolo[2,1-f][1,2,4]triazin-6-yloxy]-propan-2-one A mixture of Example 1 (3.1 g, 10 mmol), chloroacetone (1.02 g, 11 mmol), and K₂CO₃ (4.1 g, 30 mmol) in acetone (100 mL) was heated at 50° C. for 6 h. The mixture was cooled and concentrated to give a beige solid which was washed with ethyl acetate/dichloromethane (1:1). The filtrate was purified by passing through a short pad of silica gel to afford the desired product (3.34 g, 91% yield) as a light beige solid. MS: (M+H)⁺=369.

B. 2-[4-(4-Fluoro-2-methyl-1H-indol-5-yloxy)-5-methylpyrrolo[2,1-f][1,2,4]triazin-6-yloxy]-1-methylethylamine A mixture of above compound A (56 mg, 0.15 mmol), ammonium formate (100 mg, 1.6 mmol), NaBH(OAc)₃ (84 mg, 0.4 mmol), acetic acid (0.2 mL) and molecular sieves (100 mg) in THF (2 mL) was stirred at RT overnight. Another portion of ammonium formate (100 mg, 1.6 mmol) and NaBH(OAc)₃ (84 mg, 0.4 mmol) was added, and the mixture was stirred for additional 5 h. The solid was filtered and the filtrate was purified by preparative HPLC. The desired fraction was lyophilized to afford the TFA salt of the desired compound (20 mg, 28% yield) as a white solid. MS: (M+H)⁺=370

Example 74

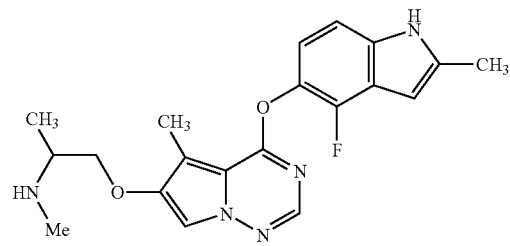

{2-[4-(4-Fluoro-2-methyl-1H-indol-5-yloxy)-5-methylpyrrolo[2,1-f][1,2,4]triazin-6-yloxy]-1-methyl-ethyl}-methylamine A mixture of compound A of Example 73 (56 mg, 0.15 mmol), methylamine (2M in THF, 0.2 mmol), NaBH(OAc)₃ (42 mg, 0.2 mmol), acetic acid (20 μL) and 3 Å molecular sieves (100 mg) in THF (2 mL) was stirred at RT for 20 h. The solids were filtered and the filtrate was purified by preparative HPLC to afford the title compound as a white solid (21 mg, 37% yield). MS: (M+H)⁺=384.

Example 75

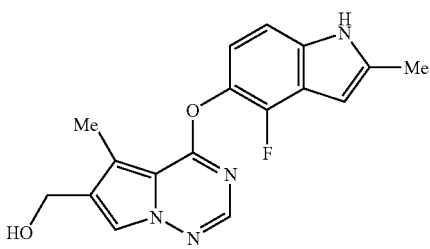

[4-(4-Fluoro-2-methyl-1H-indol-5-yloxy)-5-methylpyrrolo[2,1-f][1,2,4]triazin-6-yl]-methanol To a solution of 4-(4-fluoro-2-methyl-1H-indol-5-yloxy)-5-methyl-pyrrolo[2,1-f][1,2,4]triazine-6-carboxylic acid ethyl ester (68 mg 0.19 mmol) in anhydrous methylene chloride (2.0 mL) at −78° C. under argon was added DIBAL (0.48 mmol, 0.48 mL, 1.0M, 2.5 eq.) dropwise. After 5 minutes, the mixture was warmed to −15° C. and allowed to stir for an additional 15 minutes. A drop of ethanol was added to quench the reaction followed by 1N sodium hydroxide (0.2 mL) and 1.0 mL of ethyl acetate and 1.0 mL of THF. After 30 minutes, the mixture was filtered to remove the resulting solid. The filtrate was dried, concentrated in vacuo, and chromatographed using silica gel eluting with 40-75% ethyl acetate in hexanes (gradient). Concentration of the desired fractions afforded the title compound (39 mg, 63%) as a clear oil. LC/MS; (M+H)⁺=327.3

Example 76

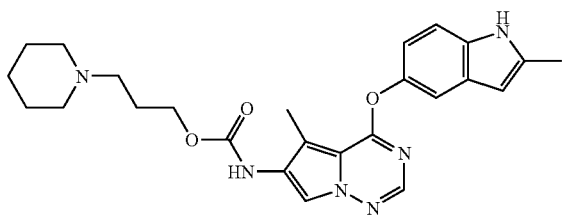

[5-Methyl-4-(2-methyl-1H-indol-5-yloxy)-pyrrolo[2,1-f][1,2,4]triazin-6-yl]-carbamic Acid 3-piperidin-1-yl-propyl Ester A. To a stirred solution of 4-chloro-5-methyl-pyrrolo[2,1-f][1,2,4]triazine-6-carboxylic acid methyl ester (0.5 g, 2.22 mmol) and 2-methyl-5-hydroxyindole (424 mg, 2.9 mmol) under argon in acetonitrile (10.0 mL) was added triethylamine (6.65 mmol, 0.93 mL). After stirring the mixture at room temperature for 17 h. solvent was removed under vacuum and the residue was chromatographed on silica gel eluting with 20-30% ethyl acetate (gradient) in hexanes. The solvent was removed in vacuo to obtain 5-methyl-4-(2-methyl-1H-indol-5-yloxy)-pyrrolo[2,1-f][1,2,4]triazine-6-carboxylic acid methyl ester as a white solid (0.58 g, 85%). LC/MS; (M+H)⁺=337.2

B. To a solution of compound A (575 mg, 1.71 mmol) in pyridine (20 mL) was added lithium iodide (17 mmol, 2.3 g). The mixture was stirred at reflux for 45 h. The mixture was allowed to cool and the pyridine was then removed in vacuo. The remaining solid material was purified by preparative HPLC. Removal of the eluent in vacuo afforded 5-methyl-4-(2-methyl-1H-indol-5-yloxy)pyrrolo[2,1-f][1,2,4]triazine-6-carboxylic acid (228 mg, 41%) as a brown solid. LC/MS; (M+H)⁺=323.1

C. To a solution of compound B (35 mg, 0.11 mmol) in dioxane (7 mL) was added ca. 5 mg of crushed 4 Å molecular sieves, triethylamine (0.13 mmol, 18 μL), and DPPA (0.13 mmol, 28 μL). The mixture was heated under argon at 50° C. for 6 h, followed by addition of the 3-piperidinepropanol (1.1 mmol, 156 mg) in dioxane (2.0 mL), warmed to 76° C., then allowed to stir for ca. 16 h. The reaction mixture was purified on preparative HPLC. The product obtained was then dissolved in ethyl acetate (100 mL) and washed with 30 mL of saturated aqueous sodium bicarbonate, dried, filtered and concentrated in vacuo. The oil was then chromatographed using silica gel eluting with 1% triethylamine, 10% methanol in chloroform. Removal of the solvent in vacuo afforded the title compound (9.2 mg, 18%) as an orange oil. LC/MS; (M+H)⁺=323.2

Example 77

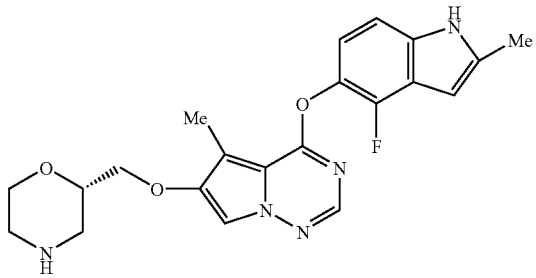

4-(4-Fluoro-2-methyl-1H-indol-5-yloxy)-5-methyl-6-(morpholin-2-ylmethoxy)-pyrrolo[2,1-f][1,2,4]triazine A. To a solution of (2S)-4-tert-butoxycarbonyl-2-hydroxymethylmorpholine [28.6 mg, 0.13 mmol, for preparation see Heterocycles (1993), 35(1), 105] and triethylamine (16 mg, 0.16 mmol) in dichloromethane (0.5 mL) at 0° C. was added methanesulfonyl chloride (18 mg, 0.157 mmol). The mixture was stirred at 0° C. for 1 h and then diluted with ethyl acetate (5 mL). The mixture was washed successively with 1 M KHSO₄ solution and brine. The organic layer was separated, dried, and was concentrated to afford crude product, 38 mg (99%) as an oil, which was used directly in the next step.

A mixture of the crude compound (38 mg, 0.13 mmol), Example 1 (45 mg, 0.14 mmol) and K₂CO₃ (50 mg, 0.36 mmol) in DMF (0.5 mL) was stirred at RT for 48 h. The mixture was diluted with dichloromethane and filtered. The filtrate was washed with water, dried and concentrated. The residue was purified by preparative HPLC to afford (2S)-2-methanesulfonyloxymethyl-morpholine-4-carboxylic acid tert-butyl ester (15 mg, 22.6%). as a gel. LC/MS; (M+H)$^+$=512.

B. Compound A (15 mg) was dissolved in 4 M HCl in dioxane (0.1 mL) at 0° C. and stirred at this temperature for 10 h and stored in a refrigerator for 72 h. The mixture was neutralized with aqueous NaHCO$_3$ solution and purified by preparative HPLC. The fraction containing the desired product was neutralized with NaHCO$_3$ and extracted with ethyl acetate. The extract was dried and concentrated, and the residue was lyophilized to afford the title compound (2 mg, 16%) as a solid. LC/MS; (M+H)$^+$=412.

Example 78

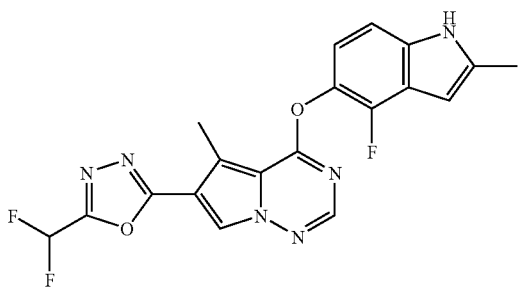

6-(5-Difluoromethyl-[1,3,4]oxadiazol-2-yl)-4-(4-fluoro-2-methyl-1H-indol-5-yloxy)-5-methylpyrrolo-[2,1-f][1,2,4]triazine A. 4-Hydroxy-5-methyl-pyrrolo[2,1-f][1,2,4]triazine-6-carboxylic acid ethyl ester (1.5 mmol, 331 mg) was dissolved in a 4:1 mixture of hydrazine in ethanol (2 mL) and the mixture was heated at 90° C. for 8 h. The mixture was cooled to RT and concentrated in vacuo to afford 4-[[2,4-difluoro-5-[(methoxyamino)carbonyl]phenyl]amino]-5-(1-methylethyl)pyrrolo[2,1-f][1,2,4]triazine-6-carboxylic acid hydrazide (300 mg, 97%) as an off-white solid.

B. Compound A (100 mg, 0.43 mmol) and difluoroacetic acid were added to phosphorous oxychloride (3 mL) and the resulting mixture was heated at 120° C. for 10 h. The reaction mixture was cooled to ambient temperature and concentrated in vacuo. The residue was partitioned between ethyl acetate and saturated NaHCO$_3$ solution. The organic layer was separated, dried (Na$_2$SO$_4$), filtered and concentrated. The resulting oily residue was then dissolved in DMF (2 mL) and 4-fluoro-2-methyl-1H-indol-5-ol (0.13 g, 0.63 mmol) and potassium carbonate were added. The resulting mixture was stirred at 50° C. for 5 h, then cooled to ambient temperature and diluted with methylene chloride. The organic layer was washed with water, dried (Na$_2$SO$_4$), filtered and concentrated. Purification by preparative HPLC afforded the title compound (22 mg, 31% overall) as a white solid. LC/MS; (M+H)$^+$=415.14.

Example 79

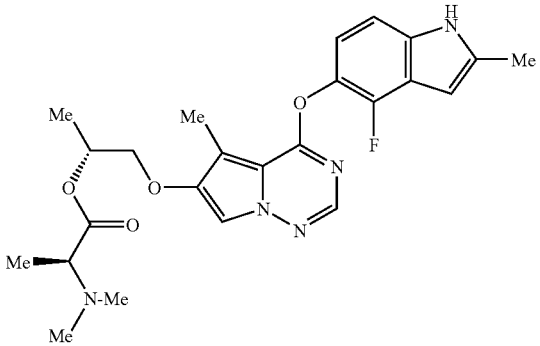

[(1R),2S]-2-Dimethylaminopropionic acid-[2-[4-(4-fluoro-2-methyl-1H-indol-5-yloxy)-5-methylpyrrolo[2,1-f]-[1,2,4]triazin-6-yloxy]]-1-methylethyl Ester A mixture of Example 15 (80 mg, 0.22 mmol), N,N-dimethyl-L-alanine (41 mg, 0.35 mmol), HATU (132 mg, 0.69 mmol), DIPEA (91 mg, 0.69 mmol), and DMAP (3 mg) in DMF (1.5 ml) was stirred for 16 h. The volatiles were removed in vacuo, and the residue was purified by preparative HPLC. The desired fraction was collected, treated with aqueous HCl (1M) and then lyophilized to afford the title compound (69 mg, 63% yield) as a white solid. LC/MS; (M+H)$^+$=470. $^1$HNMR (CD$_3$OD): □ 1.45 (d, 3H, J=6.6 Hz); 2.43 (s, 3H); 2.45 (s, 3H); 2.98 (s, 6H); 3.65 (s, 2H); 4.19 (d, 2H, J=2.75 Hz); 5.10 (m 1H); 6.23 (s, 1H); 6.90 (m, 1H); 7.10 (d, 1H); 7.66 (s, 1H), 7.75 (s, 1H).

Example 80

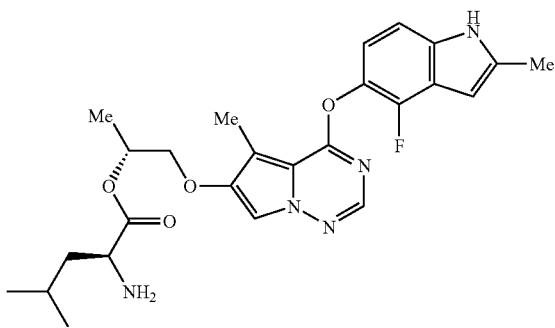

[(1R),2S]-2-Amino-4-methylpentanoic Acid [2-[4-(4-fluoro-2-methyl-1H-indol-5-yloxy)-5-methylpyrrolo[2,1-f][1,2,4]triazin-6-yloxy]]-1-methylethyl Ester Step A A mixture of Example 15 (93 mg, 0.3 mmol), N-Cbz-L-leucine (159 mg, 0.6 mmol), HATU (228 mg, 0.6 mmol), DIPEA (154 mg, 1.2 mmol), and DMAP (5 mg) in DMF (1.5 mL) was stirred overnight. The volatiles were removed in vacuo, and the residue was purified by preparative HPLC to afford 2-benzyloxycarbonylamino-4-methylpentanoic acid [2-[4-(4-fluoro-2-methyl-1H-indol-5-yloxy)-5-methylpyrrolo[2,1-f][1,2,4]triazin-6-yloxy]]-1-methylethyl ester as a white solid (145 mg, 78% yield as a single diastereomer).

Step B

The compound from step A above (130 mg, 0.21 mmol), Pd/C (10%, 26 mg) and ammonium formate (400 mg) in DMF (4 mL) were stirred at RT for 4 h. The mixture was diluted with ethyl acetate, filtered through a pad of Celite®, and concentrated. The residue was purified by preparative HPLC. The desired fraction was collected, mixed with 1 N aqueous HCl and lyophilized to afford the title compound as a white solid (92 mg, 84% yield). MS: (M+H)$^+$=484. $^1$HNMR (CD$_3$OD): □ 0.99 (m, 6H), 1.45 (d, 3H, J=8.2 Hz), 1.70 (m, 1H), 1.80 (m, 2H), 2.44 (s, 3H), 2.46 (s, 3H), 4.03 (t, 1H), 4.20 (d, 2H, J=4.40 Hz), 5.45 (m 1H), 6.23 (s, 1H), 6.90 (m, 1H), 7.11 (d, 1H, J=10.4 Hz), 7.67 (s, 1H), 7.75 (s, 1H).

Example 81

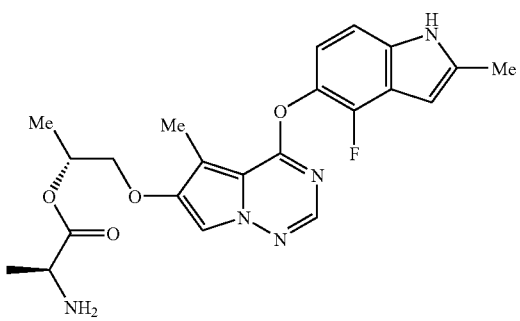

[(1R),2S]-2-Aminopropionic acid 2-[4-(4-fluoro-2-methyl-1H-indol-5-yloxy)-5-methylpyrrolo[2,1-f][1,2,4]triazin-6-yloxy]-1-methylethyl Ester Step A A mixture of Example 15 (60 mg, 0.0.16 mmol), N-Cbz-L-alanine (89 mg, 0.4 mmol), HATU (253 mg, 0.4 mmol), DIPEA (103 mg, 0.8 mmol), and DMAP (5 mg) in DMF (1 mL) was stirred overnight. The volatiles were removed in vacuo, and the residue was purified by preparative HPLC to afford homochiral 2-benzyloxycarbonylamino-propionic acid [2-[4-(4-fluoro-2-methyl-1H-indol-5-yloxy)-5-methylpyrrolo[2,1-f][1,2,4]triazin-6-yloxy]]-1-methylethyl ester as a white solid (77 mg, 84% yield).

Step B

A mixture of the compound from step A above (60 mg, 0.11 mmol), Pd/C (6 mg), and ammonium formate (200 mg) in DMF (1.5 mL) were stirred at RT for 30 min. The mixture was diluted with ethyl acetate, and then filtered through a pad of Celite®. The filtrate was washed with water, dried over Na$_2$SO$_4$, and concentrated. The product was mixed with 1 N aqueous HCl and lyophilized to afford the title compound as a white solid (53 mg, 99% yield). MS: (M+H)$^+$=442. $^1$HNMR (CD$_3$OD): □ 1.45 (d, 3H, J=6.60 Hz), 1.56 (d, 3H, J=7.47 Hz), 2.44 (s, 3H), 2.46 (s, 3H), 4.13 (q, 1H), 4.18 (d, 2H, J=3.96 Hz), 5.45 (m 1H); 6.23 (s, 1H); 6.90 (dd, 1H); 7.10 (d, 1H); 7.66 (s, 1H), 7.75 (s, 1H).

Example 82

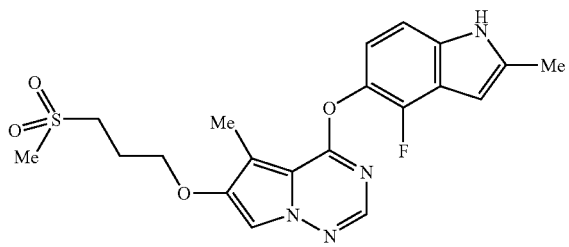

4-(4-Fluoro-2-methyl-1H-indol-5-yloxy)-6-(3-methanesulfonyl-propoxy)-5-methylpyrrolo[2,1-f][1,2,4]triazine A. To a solution of 4-phenoxy-5-methyl-6-hydroxypyrrolo-[2,1-f][1,2,4]triazine (1.0 g, 4.15 mmol, as prepared in WO 00/71129, which is hereby incorporated by reference), 3-methanesulfonylpropan-1-ol (1.15 g, 8.3 mmol) and PPh$_3$ (2.17 g, 8.3 mmol) in THF (12 mL) at 0° C., was added DEAD (1.42 g, 8.3 mmol). The mixture was stirred at RT for 1 h. The solvent was removed in vacuo. The residue was dissolved in dichloromethane, washed with brine and dried (Na$_2$SO$_4$). The volatiles were removed and the solid obtained was triturated with dichloromethane to afford 6-(3-methanesulfonyl-propoxy)-5-methyl-4-phenoxypyrrolo[2,1-f][1,2,4]triazine as a white solid (1.1 g, 73% yield). MS: (M+H)$^+$=362.

B. A mixture of 6-(3-methanesulfonyl-propoxy)-5-methyl-4-phenoxypyrrolo[2,1-f][1,2,4]triazine (1.1 g, 3.04 mmol), HCl (1N, 20 mL) and ethanol (20 mL) was heated at 80° C. for 3 h. The volatiles were removed in vacuo. The white solid was triturated with diethyl ether/hexane (2:1) to afford 6-(3-methanesulfonyl-propoxy)-5-methylpyrrolo[2,1-f][1,2,4]triazin-4-ol (820 mg, 95%) as a white solid MS: (M+H)$^+$=286.

C. A mixture of 6-(3-methanesulfonyl-propoxy)-5-methylpyrrolo[2,1-f][1,2,4]triazin-4-ol (620 mg, 2.17 mmol) and POCl$_3$ (10 mL) was heated at 85° C. for 3 h. POCl$_3$ was removed in vacuo to give a yellow solid, which was dissolved in dichloromethane, and washed successively with cold NaHCO$_3$ solution and brine. The organics were dried, filtered and concentrated to afford the crude chloroimidate intermediate (610 mg), which was added to a pre-mixed solution of 4-fluoro-2-methyl-1H-indol-5-ol (664 mg, 4.02 mmol) and NaH (60% in mineral oil, 160 mg, 4.02 mmol) in DMF at 0° C. The resulting mixture was stirred at RT for 30 min, and diluted with dichloromethane, washed with 10% LiCl aqueous solution, dried concentrated. The residue was purified by flash column chromatography (silica gel, eluting from 10% ethyl acetate/dichloromethane to 30% ethyl acetate/dichloromethane). The desired fractions were combined and concentrated in vacuo to give a solid, which was washed with MeOH to afford the title compound as a white solid (610 mg, 65% yield). HRMS (M+H)$^+$ Calcd. For C$_{20}$H$_{21}$FN$_4$O$_4$S: 432.12675. Found: 433.1329. $^1$H NMR (d-DMSO) δ 11.36 (br, 1H), 7.94 (s, 1H), 7.93 (s, 1H), 7.15 (d, 1H, J=8.4 Hz), 6.99 (m, 1H), 6.24 (s, 1H), 4.16 (t, 2H, J=6.16 Hz), 3.31 (t, 2H, J=5.7 Hz), 3.05 (s, 3H), 2.42 (s, 3H), 2.41 (s, 3H), 2.50

(m, 2H). Anal. Calcd. For $C_{20}H_{21}FN_4O_4S$: 0.4$H_2O$: C, 54.58; H, 4.84; N, 12.56; S 7.29. Found: C, 54.61; H, 4.92; N, 12.65; S 7.33.

Example 83

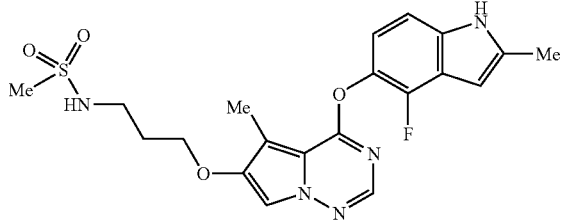

N-{3-[4-(4-Fluoro-2-methyl-1H-indol-5-yloxy)-5-methylpyrrolo[2,1-f][1,2,4]triazin-6-yloxy]-propyl}-methanesulfonamide A. A solution of 4-phenoxy-5-methyl-6-hydroxypyrrolo[2,1-f][1,2,4]triazine (1.05 g, 4.35 mmol), 1,3-dibromopropane (4.0 g, 20 mmol), and $K_2CO_3$ (3 g, 22 mmol) was heated at 70° C. for 2 h. The solvent was removed in vacuo. The residue was purified by flash column chromatography (silica gel, eluting from dichloromethane to 20% ethyl acetate/dichloromethane) to afford the crude intermediate (1.35 g, 86% yield). This intermediate (1.3 g, 3.59 mmol) was heated with methanesulfonamide (2.0 g, 21 mmol) and $K_2CO_3$ (4 g, 29 mmol) in DMF (15 mL) for 2 h. The mixture was cooled, diluted with dichloromethane, washed twice with 5% $Na_2CO_3$ solution, dried and concentrated. The residue was purified by flash column chromatography (silica gel, 20% ethyl acetate/dichloromethane) to afford N-[3-(5-methyl-4-phenoxy-pyrrolo[2,1-f][1,2,4]triazin-6-yloxy)-propyl]-methanesulfonamide (1.1 g, 81%) as a white solid. MS: (M+H)$^+$=377.

B. The compound from Step A above was treated with methanesulfonamide by a procedure similar to that described for the preparation of Example 24 to obtain N-[3-(4-hydroxy-5-methylpyrrolo[2,1-f][1,2,4]triazin-6-yloxy)-propyl]-methanesulfonamide. (64% yield). MS: (M+H)$^+$=301.

C. A mixture of N-[3-(4-hydroxy-5-methylpyrrolo[2,1-f][1,2,4]triazin-6-yloxy)-propyl]-methanesulfonamide (530 mg, 1.77 mmol) and $POCl_3$ was heated at 80° C. for 1.5 h. The volatiles were removed and the residue was diluted with dichloromethane, washed successively with cold $NaHCO_3$ solution and brine, dried, and concentrated in vacuo to afford the crude chloroimidate intermediate (610 mg), which was heated with 4-fluoro-2-methyl-1H-indol-5-ol (495 mg, 3.0 mmol) and $K_2CO_3$ (3.0 g, 22 mmol) in DMF (8 mL) at 80-85° C. for 2 h. The mixture was diluted with dichloromethane and the solid was filtered. The filtrate was concentrated and the residue was purified by silica gel flash column chromatography eluting with 30% ethyl acetate/dichloromethane. The desired product was further purified by preparative HPLC to afford the title compound (290 mg, 34% yield) as a tan solid. HRMS (M+H)$^+$ Calcd. For $C_{20}H_{22}FN_5O_4S$: 447.1376. Found: 448.1476. $^1$H NMR (CDCl$_3$) δ7.75 (s, 1H), 7.24 (s, 1H), 7.03 (d, 1H, J=8.32 Hz), 6.88 (m, 1H), 4.04 (t, 2H, J=5.72 Hz), 3.31 (t, 2H, J=6.16 Hz), 2.90 (s, 3H), 2.42 (s, 3H), 2.37 (s, 3H), 2.04 (m, 2H). Anal. Calcd. For $C_{20}H_{21}FN_4O_4S$: 1.0$H_2O$:0.18 TFA: C, 50.57; H, 4.73; N, 14.61; S 6.80. Found: C, 50.44; H, 4.87; N, 14.51; S 6.70.

What is claimed is:

1. A compound having the formula

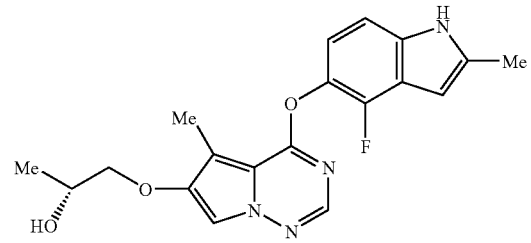

or a pharmaceutically acceptable salt thereof.

2. A pharmaceutical composition comprising the compound according to claim 1 and a pharmaceutically acceptable carrier.

3. A method for treating a VEGFR-2 and/or FGFR-1 related cancer in a mammal in need thereof comprising administering to said mammal a therapeutically effective amount of a compound having the formula

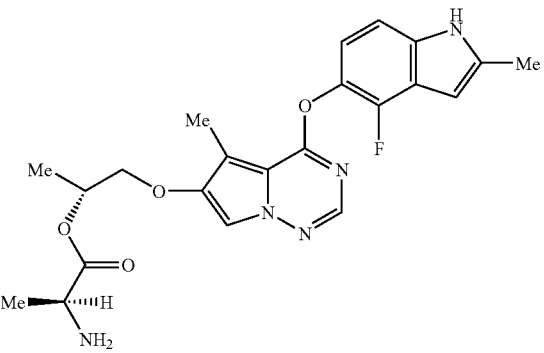

or a pharmaceutically acceptable salt thereof, wherein the cancer is hepatocellular cancer, colorectal cancer or non-small cell lung cancer.

4. A method for treating a VEGFR-2 and/or FGFR-1 related cancer in a mammal in need thereof comprising treating said mammal with a therapeutically effective amount of a compound having the formula

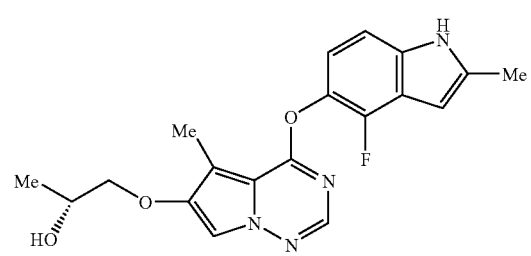

or a pharmaceutically acceptable salt thereof, wherein the cancer is hepatocellular cancer, colorectal cancer or non-small cell lung cancer.

* * * * *